(12) United States Patent
Dweik et al.

(10) Patent No.: US 11,004,568 B2
(45) Date of Patent: *May 11, 2021

(54) SYSTEMS AND METHODS FOR MULTI-DIMENSIONAL FLUID MODELING OF AN ORGANISM OR ORGAN

(71) Applicant: Altair Engineering, Inc., Troy, MI (US)

(72) Inventors: Zain S. Dweik, Hamilton, OH (US); Shane Cline, Evendale, OH (US)

(73) Assignee: Altair Engineering, Inc., Troy, MI (US)

( * ) Notice: Subject to any disclaimer, the term of this patent is extended or adjusted under 35 U.S.C. 154(b) by 376 days.

This patent is subject to a terminal disclaimer.

(21) Appl. No.: 15/630,935

(22) Filed: Jun. 22, 2017

(65) Prior Publication Data

US 2018/0260532 A1  Sep. 13, 2018

Related U.S. Application Data

(60) Provisional application No. 62/469,953, filed on Mar. 10, 2017.

(51) Int. Cl.
*G06F 3/0481* (2013.01)
*G16H 50/50* (2018.01)
(Continued)

(52) U.S. Cl.
CPC ......... *G16H 50/50* (2018.01); *G05B 13/0265* (2013.01); *G05B 13/041* (2013.01);
(Continued)

(58) Field of Classification Search
None
See application file for complete search history.

(56) References Cited

U.S. PATENT DOCUMENTS 8,526,701 B2    9/2013  Razifar et al.
8,548,828 B1 *  10/2013 Longmire .............. G06Q 10/10
                                                    705/3
(Continued)

FOREIGN PATENT DOCUMENTS

WO    2016/038208 A2    3/2016
WO    2017/188858 A1    11/2017
WO    2018/117890 A1    6/2018

OTHER PUBLICATIONS

Final Office Action received for U.S. Appl. No. 15/627,105 dated Jan. 16, 2020, 26 pages.
(Continued)

*Primary Examiner* — Kibrom K Gebresilassie
(74) *Attorney, Agent, or Firm* — Fish & Richardson P.C.

(57) ABSTRACT

A multiple fluid model tool for multi-dimensional fluid modeling of a biological structure is presented. For example, a system includes a modeling component, a machine learning component, and a three-dimensional health assessment component. The modeling component generates a three-dimensional model of a biological structure based on multi-dimensional medical imaging data. The machine learning component predicts one or more characteristics of the biological structure based on input data and a machine learning process associated with the three-dimensional model. The three-dimensional health assessment component that provides a three-dimensional design environment associated with the three-dimensional model. The three-dimensional design environment renders physics modeling data of the biological structure based on the input data and the one or more characteristics of the biological structure on the three-dimensional model.

20 Claims, 14 Drawing Sheets
(1 of 14 Drawing Sheet(s) Filed in Color)

(51) Int. Cl.
*G06F 19/00* (2018.01)
*G06N 20/00* (2019.01)
*G16H 30/40* (2018.01)
*G06F 30/17* (2020.01)
*G06F 30/20* (2020.01)
*G05B 13/02* (2006.01)
*G05B 13/04* (2006.01)
*G05D 7/06* (2006.01)
*G06N 5/04* (2006.01)
*G16H 50/20* (2018.01)
*G01F 5/00* (2006.01)

(52) U.S. Cl.
CPC ......... *G05B 13/048* (2013.01); *G05D 7/0617* (2013.01); *G06F 3/04815* (2013.01); *G06F 19/321* (2013.01); *G06F 30/17* (2020.01); *G06F 30/20* (2020.01); *G06N 5/04* (2013.01); *G06N 20/00* (2019.01); *G16H 30/40* (2018.01); *G01F 5/00* (2013.01); *G16H 50/20* (2018.01); *Y02T 90/00* (2013.01)

(56) References Cited

U.S. PATENT DOCUMENTS

| | | | |
|---|---|---|---|
| 8,970,592 B1* | 3/2015 | Petterson | G06T 13/60 345/419 |
| 9,014,485 B2* | 4/2015 | Moehrle | G06F 19/321 382/209 |
| 9,347,288 B2 | 5/2016 | Clemens et al. | |
| 9,760,690 B1* | 9/2017 | Petkov | G06T 15/08 |
| 9,836,885 B1 | 12/2017 | Eraker et al. | |
| 9,916,538 B2 | 3/2018 | Zadeh et al. | |
| 10,198,550 B2 | 2/2019 | Lutich | |
| 10,237,567 B2 | 3/2019 | Nguyen et al. | |
| 10,237,587 B2 | 3/2019 | Rea Zanabria et al. | |
| 10,280,722 B2 | 5/2019 | Bello et al. | |
| 10,380,809 B2 | 8/2019 | Pereira | |
| 10,409,950 B2 | 9/2019 | Dweik | |
| 10,650,114 B2 | 5/2020 | Dweik | |
| 10,803,211 B2* | 10/2020 | Dweik | G06F 30/13 |
| 10,867,085 B2* | 12/2020 | Dweik | G06F 30/20 |
| 2008/0129732 A1* | 6/2008 | Johnson | G06T 7/0002 345/424 |
| 2009/0204245 A1 | 8/2009 | Sustaeta et al. | |
| 2009/0312956 A1 | 12/2009 | Zombo et al. | |
| 2010/0180236 A1 | 7/2010 | Lin et al. | |
| 2010/0332373 A1 | 12/2010 | Crabtree et al. | |
| 2011/0115787 A1 | 5/2011 | Kadlec | |
| 2012/0191432 A1 | 7/2012 | Khataniar et al. | |
| 2012/0330869 A1 | 12/2012 | Durham | |
| 2013/0116996 A1 | 5/2013 | Callan | |
| 2013/0124166 A1 | 5/2013 | Clemens et al. | |
| 2013/0124176 A1 | 5/2013 | Fox et al. | |
| 2013/0346047 A1 | 12/2013 | Fukushige et al. | |
| 2014/0005994 A1* | 1/2014 | O'Brien | G06G 7/57 703/9 |
| 2014/0050406 A1 | 2/2014 | Buehler et al. | |
| 2014/0201126 A1 | 7/2014 | Zadeh et al. | |
| 2014/0207424 A1 | 7/2014 | Singh et al. | |
| 2014/0277939 A1* | 9/2014 | Ren | G01C 21/3638 701/36 |
| 2014/0280065 A1 | 9/2014 | Cronin et al. | |
| 2014/0281712 A1 | 9/2014 | Subbu et al. | |
| 2015/0066929 A1 | 3/2015 | Satzke et al. | |
| 2015/0068703 A1 | 3/2015 | de Bock et al. | |
| 2016/0044193 A1 | 2/2016 | Wells, II | |
| 2016/0044195 A1 | 2/2016 | Murrell et al. | |
| 2016/0235381 A1 | 8/2016 | Scanlan et al. | |
| 2016/0281494 A1 | 9/2016 | Shirdel et al. | |
| 2016/0284122 A1 | 9/2016 | Tatourian et al. | |
| 2016/0312552 A1 | 10/2016 | Early et al. | |
| 2017/0053463 A1 | 2/2017 | Pereira | |
| 2017/0169620 A1* | 6/2017 | Bleiweiss | G06F 17/50 |
| 2017/0220887 A1 | 8/2017 | Fathi et al. | |
| 2017/0346817 A1 | 11/2017 | Gordon et al. | |
| 2017/0357828 A1 | 12/2017 | Phillips | |
| 2018/0085927 A1 | 3/2018 | Kapoor et al. | |
| 2018/0095450 A1 | 4/2018 | Lappas et al. | |
| 2018/0120813 A1* | 5/2018 | Coffman | G06N 20/00 |
| 2018/0165418 A1* | 6/2018 | Swartz | G16H 50/30 |
| 2018/0165604 A1 | 6/2018 | Minkin et al. | |
| 2018/0204111 A1 | 7/2018 | Zadeh et al. | |
| 2018/0239874 A1* | 8/2018 | Ingram | G16H 50/30 |
| 2018/0259978 A1* | 9/2018 | Dweik | G05B 13/0265 |
| 2018/0260501 A1 | 9/2018 | Dweik et al. | |
| 2018/0260502 A1* | 9/2018 | Dweik | G06F 30/13 |
| 2018/0260503 A1 | 9/2018 | Dweik et al. | |
| 2018/0260513 A1 | 9/2018 | Dweik | |
| 2018/0330028 A1 | 11/2018 | Nutt et al. | |
| 2018/0351635 A1 | 12/2018 | Westervelt et al. | |
| 2018/0354641 A1 | 12/2018 | de Bock et al. | |
| 2018/0371874 A1* | 12/2018 | Shetty | E21B 49/08 |
| 2019/0050506 A1* | 2/2019 | Umetani | G06F 17/5009 |
| 2019/0114751 A1* | 4/2019 | Suzuki | G06T 15/08 |
| 2019/0244363 A1* | 8/2019 | Tan | G06T 15/08 |

OTHER PUBLICATIONS

Non-Final Office Action received for U.S. Appl. No. 15/627,068 dated Dec. 26, 2019, 42 pages.
Final Office Action received for U.S. Appl. No. 15/630,941 dated Dec. 27, 2019, 42 pages.
Extended European Search Report received for EP Patent Application Serial No. 18160269.9 dated Jul. 16, 2018, 9 pages.
Non-Final Office Action received for U.S. Appl. No. 15/627,105 dated Jun. 13, 2019, 16 pages.
Extended European Search Report received for EP Patent Application Serial No. 18160923.1 dated Jun. 13, 2018, 9 pages.
Non-Final Office Action received for U.S. Appl. No. 15/627,068 dated Jun. 27, 2019, 16 pages.
Non-Final Office Action received for U.S. Appl. No. 15/630,941 dated Aug. 3, 2018, 27 pages.
Final Office Action received for U.S. Appl. No. 15/630,941 dated Jan. 30, 2019, 29 pages.
Non-Final Office Action received for U.S. Appl. No. 15/630,941 dated Aug. 2, 2019, 30 pages.
Non-Final Office Action received for U.S. Appl. No. 15/630,939 dated Oct. 18, 2018, 20 pages.
Extended European Search Report received for EP Patent Application Serial No. 18160270.7 dated Jul. 16, 2018, 9 pages.
Non-Final Office Action received for U.S. Appl. No. 16/517,154 dated Aug. 22, 2019, 36 pages.
Communication pursuant to Article 94(3) EPC received for EP Patent Application Serial No. 18160923.1 dated Jul. 5, 2019, 6 pages.
Notice of Allowance received for U.S. Appl. No. 15/627,105 dated Jun. 11, 2020, 21 pages.
Final Office Action received for U.S. Appl. No. 15/627,068 dated Jun. 10, 2020, 14 pages.
Non-Final Office Action received for U.S. Appl. No. 15/630,941 dated Jun. 23, 2020, 39 pages.
Non-Final Office Action received for U.S. Appl. No. 15/630,931 dated Jul. 1, 2020, 217 pages.
Non-Final Office Action received for U.S. Appl. No. 16/856,392 dated Jun. 11, 2020, 40 pages.

* cited by examiner

SYSTEMS AND METHODS FOR MULTI-DIMENSIONAL FLUID MODELING OF AN ORGANISM OR ORGAN

CROSS-REFERENCE

This application claims priority to U.S. Provisional Patent Application No. 62/469,953, filed Mar. 10, 2017, and entitled "A MULTIPLE FLUID MODEL TOOL FOR INTERDISCIPLINARY FLUID MODELING", the entirety of which application is hereby incorporated by reference herein.

TECHNICAL FIELD

This disclosure relates generally to three dimensional modeling systems, and more specifically, to modeling of a biological fluid system.

BACKGROUND

During a medical procedure associated with a biological structure, it is often desirable to determine impact of a fluid with respect to the biological structure. To determine impact of the fluid with respect to the biological structure, numerical analysis of two dimensional (2D) medical data associated with the biological structure. For instance, magnetic resonance imaging and/or computerized tomography imaging can be employed to determine impact of the fluid with respect to the biological structure. However, analyzing impact of a fluid with respect to a biological structure generally involves human interpretation of 2D medial data associated with the biological structure, which can result in human trial and error with respect to analysis of the biological structure. Moreover, human interpretation of 2D medical data can be burdensome with respect to cost and/or redundancy associated with analysis of the biological structure.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

In accordance with an embodiment, a system includes a modeling component, a machine learning component, and a three-dimensional health assessment component. The modeling component generates a three-dimensional model of a biological structure based on multi-dimensional medical imaging data. The machine learning component predicts one or more characteristics of the biological structure based on input data and a machine learning process associated with the three-dimensional model. The three-dimensional health assessment component provides a three-dimensional design environment associated with the three-dimensional model. The three-dimensional design environment renders physics modeling data of the biological structure based on the input data and the one or more characteristics of the biological structure on the three-dimensional model.

In accordance with another embodiment, a method provides for generating, by a system comprising a processor, a three-dimensional model of a biological structure based on multi-dimensional medical imaging data. The method also provides for predicting, by the system, fluid flow and physics behavior associated with the three-dimensional model based on input data and a machine learning process associated with the three-dimensional model. Furthermore, the method provides for rendering, by the system, physics modeling data of the biological structure based on the fluid flow and the physics behavior.

In accordance with yet another embodiment, a computer readable storage biological structure comprising instructions that, in response to execution, cause a system comprising a processor to perform operations, comprising: generating a three-dimensional model of a biological structure based on multi-dimensional medical imaging data, performing a machine learning process associated with the three-dimensional model to predict one or more characteristics of the biological structure, and providing a three-dimensional design environment associated with the three-dimensional model that renders physics modeling data of the biological structure based on the machine learning process.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

The patent or application file contains at least one drawing executed in color. Copies of this patent or patent application publication with color drawings will be provided by the Office upon request and payment of the necessary fee. Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
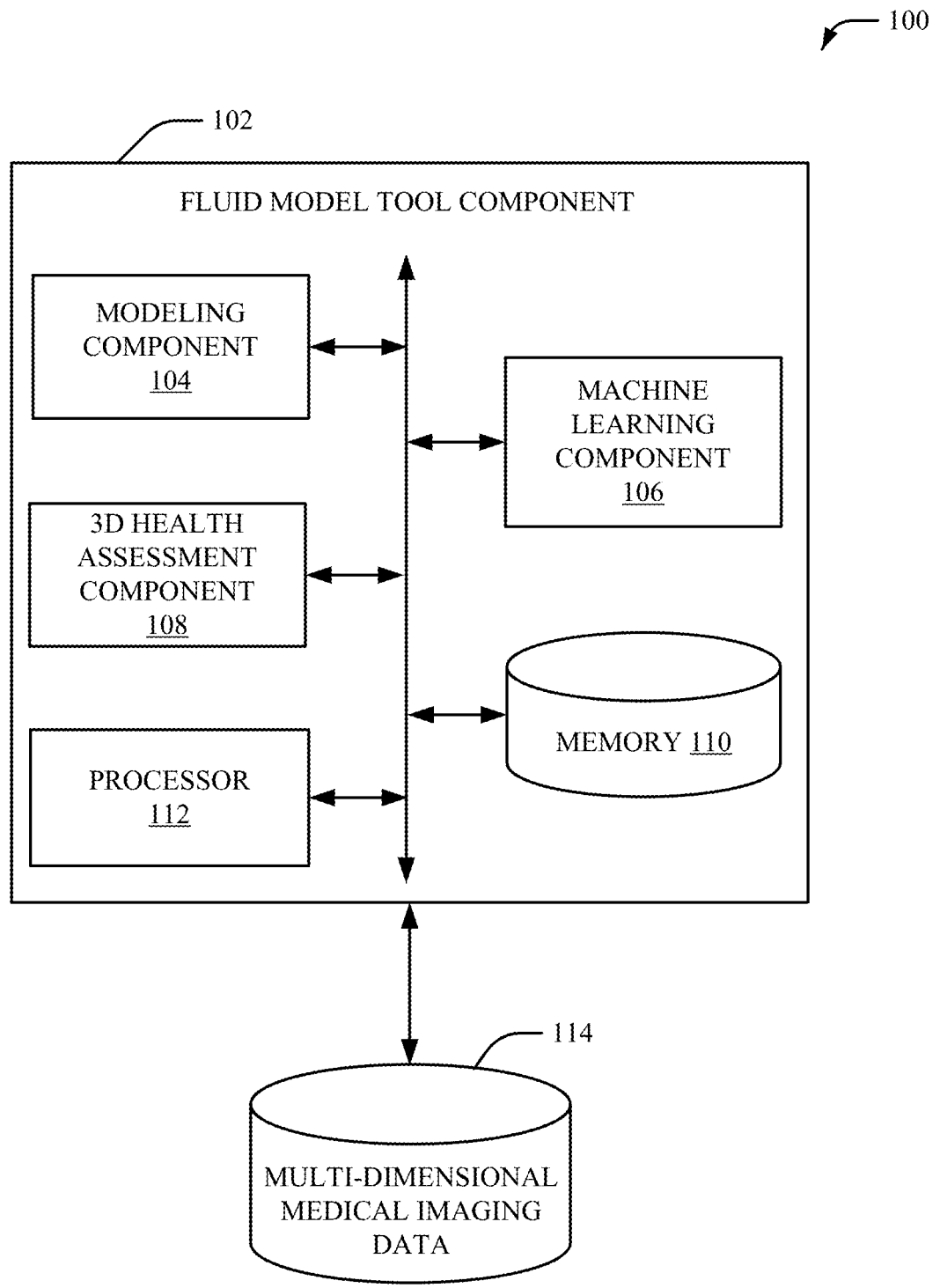
FIG. 1 illustrates a high-level block diagram of an example fluid model tool component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and biological structures are shown in block diagram form to facilitate describing one or more aspects.

Systems and techniques that provide multi-dimensional fluid modeling of an organism or organ are presented. For example, as compared to conventional analysis of an organism or organ that involves human interpretation of two-dimensional (2D) medical data and/or human trial and error with respect to analysis of an organism or organ, the subject innovations provide for a three-dimensional (3D) health assessment environment that can be generated from multi-dimensional medical imaging data. In an aspect, physics modeling data associated with a degree of fluid flow through an organism or organ can be rendered on a 3D model of the organism or organ. In one example, visual characteristics of the physics modeling data can be dynamic based on the degree of fluid flow with respect to the organism or organ. Various systems and techniques disclosed herein can be related to cloud-based services, a medical system, a health assessment system, a health diagnostic system, a medical testing system, medical imaging systems, computer processing systems, computed tomography systems, magnetic resonance imaging systems, explicit and/or implicit training of 3D models through real-time aggregation of data, etc. In an embodiment, a multiple fluid model tool can provide multi-dimensional fluid modeling of a biological structure (e.g., an organism, an organ, etc.). The multi-dimensional fluid modeling by the multiple fluid model tool can provide modeling fluid behavior in the biological structure. For instance, the multi-dimensional fluid modeling can simulate blood movement and/or waste removal through a biological structure. In one example, the multi-dimensional fluid modeling can simulate blood movement in a liver showing blood flow and waste removal by the liver. In an embodiment, markers within blood, water or another fluid can be deployed and data can be collected to generate a real-time model of a biological structure associated with a patient. Comparisons and/or analyses can be performed to assess health of the biological structure associated with the patient, provide treatment for the biological structure associated with the patient, provide predictions for the biological structure associated with the patient, provide a diet plan for the patient, determine surgery information with respect to the biological structure associated with the patient, determine medicines with respect to the biological structure associated with the patient, etc. Moreover, blood viscosity, drug efficacy, fluid dynamics, arterial strength, arterial blockage, and/or other medical characteristics can be determined or inferred with high accuracy by employing the multi-dimensional fluid modeling by the multiple fluid model tool. As such, a 3D model of a biological structure associated with physics modeling can be generated more efficiently and/or data provided by a 3D model of a biological structure associated with physics modeling can be more accurate. Moreover, damage to a biological structure associated with a 3D model can be minimized by replacing human trial and error for analyzing one or more characteristics associated with the 3D model of the biological structure.

Referring initially to FIG. 1, there is illustrated an example system 100 that provides multi-dimensional fluid modeling of a biological structure (e.g., an organism, an organ, etc.), according to an aspect of the subject disclosure. The system 100 can be employed by various systems, such as, but not limited to modeling systems, biological structure systems, cloud-based systems, medical systems, diagnostics systems, prognostics systems, medical biological structure systems, medical imaging systems, medical modeling systems, health assessment systems, simulation systems, enterprise systems, enterprise imaging solution systems, medical testing systems, advanced medical tool systems, artificial intelligence systems, machine learning systems, neural network systems, and the like. In one example, the system 100 can be associated with a graphical user interface system to facilitate visualization and/or interpretation of 3D data. Moreover, the system 100 and/or the components of the system 100 can be employed to use hardware and/or software to solve problems that are highly technical in nature (e.g., related to processing 3D data, related to modeling 3D data, related to artificial intelligence, etc.), that are not abstract and that cannot be performed as a set of mental acts by a human.

The system 100 can include a fluid model tool component 102 that can include a modeling component 104, a machine learning component 106 and/or a 3D health assessment component 108. In an aspect, modeling performed by the fluid model tool component 102 can be associated with a flow integrated health assessment environment, a heat transfer health assessment environment and/or a combustion health assessment environment. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing biological structure(s), virtual machine(s), etc. can cause the machine(s) to perform the operations described. The system 100 (e.g., the fluid model tool component 102) can include memory 110 for storing computer executable components and instructions. The system 100 (e.g., the fluid model tool component 102) can further include a processor 112 to facilitate operation of the instructions (e.g., computer executable components and instructions) by the system 100 (e.g., the fluid model tool component 102). In certain embodiments, the system 100 can further include multi-dimensional medical imaging data 114.

The modeling component 104 can generate a 3D model of a biological structure. The biological structure can be, for example, an organ, an organism, an anatomical structure, another type of biological entity, etc. In an aspect, the biological structure can be an anatomical structure of a patient body. The 3D model can be a 3D representation of the biological structure for presentation via a 3D health assessment environment. The modeling component 104 can generate the 3D model of the biological structure based on, for example, the multi-dimensional medical imaging data 114. The multi-dimensional medical imaging data 114 can be, for example, 3D medical imaging data associated with one or more medical imaging biological structures. For instance, the multi-dimensional medical imaging data 114 can be a set of consecutive images and/or a set of data that is repeatedly captured via a set of sensors (e.g., a set of sensors associated with a medical imaging biological structure) during an interval of time. The multi-dimensional medical imaging data 114 can be received directly from one or more medical imaging biological structures. Alternatively, the multi-dimensional medical imaging data 114 can be stored in one or more databases that receives and/or stores the multi-dimensional medical imaging data 114 associated with the one or more medical imaging biological structures. A medical imaging biological structure can be, for example, a computed tomography (CT) biological structure, a magnetic resonance imaging (MRI) biological structure, a positron emission tomography (PET) biological structure, a computed axial tomography (CAT) biological structure, an ultrasound biological structure, another type of medical imaging biological structure, etc. In an aspect, the multi-dimensional medical imaging data 114 can be rendered from one or more 2D images. For example, the multi-dimensional medical imaging data 114 can be rendered into 3D medical imaging data from 2D medical imaging data (e.g., 2D CT imaging data, 2D MRI imaging data, etc.). Additionally or alternatively, the multi-dimensional medical imaging data 114 can be generated based on one or more 3D sensor associated with one or more 3D imaging biological structures. In an aspect, the 3D model generated by the modeling component 104 can be a multi-dimensional mesh model (e.g., a 3D mesh model). For instance, the 3D model generated by the modeling component 104 can include polygons, vectors, vertices, edges and/or faces associated with the multi-dimensional medical imaging data 114. The multi-dimensional medical imaging data 114 can also provide a mapping of the biological structure.

In certain embodiments, the modeling component 104 can determine a set of boundaries for features of the biological structure. Furthermore, the modeling component 104 can determine a set of physical characteristics for the biological structure. In a non-limiting example, the modeling component 104 can determine one or more chambers of the biological structure. The modeling component 104 can, for example, determine a set of boundaries that define the one or more chambers. The modeling component 104 can also determine a set of physical characteristics for the one or more chambers such as, for example, a size for the one or more chambers, a shape for the one or more chambers, a volume of the one or more chambers and/or another physical characteristic for the one or more chambers. In an aspect, the modeling component 104 can employ one or more modeling techniques using the multi-dimensional medical imaging data 114. As such, the one or more physical features of the biological structure computationally derived. In another aspect, the modeling component 104 can perform a modeling process associated with the one or more modeling techniques to facilitate health assessment of the biological structure.

In an embodiment, the modeling component 104 can determine a set of control volumes associated with the biological structure. For instance, the modeling component 104 can overlay a set of control volumes on the biological structure. A control volume can be an abstraction of a region of the biological structure through which a fluid (e.g., a liquid or a gas) flows. In one example, a control volume can correspond to a chamber or a vessel of the biological structure. The modeling component 104 can determine geometric features of the set of control volumes. For instance, the modeling component 104 can determine computational control volumes (e.g., chambers) and/or geometrical features of the computational control volumes. Control volumes can be connected via various types of elements and/or sub-components to construct an analysis computational model of the biological structure that extends from supply to sink conditions. Control volumes can also simulate run conditions for the biological structure associated with the 3D model. In an aspect, the modeling component 104 can integrate a first flow network associated with a first portion of the biological structure with a second flow network associated with a second portion of the biological structure. Additionally or alternatively, the modeling component 104 can integrate first heat transfer throughout a first portion of the biological structure with second heat transfer throughout a second portion of the biological structure.

The machine learning component 106 can perform learning (e.g., explicit learning and/or implicit learning) and/or can generate inferences with respect to one or more 3D models generated by the modeling component 104. The learning and/or generated inferences by the machine learning component 106 can facilitate determination of one or more characteristics associated with the one or more 3D models generated by the modeling component 104. The learning and/or generated inferences can be determined by the machine learning component 106 via one or more machine learning processes associated with the one or more 3D models. The one or more characteristics determined by the machine learning component 106 can include, for example, one or more fluid characteristics associated with the one or more 3D models generated by the modeling component 104, one or more thermal characteristics associated with the one or more 3D models generated by the modeling component 104, one or more combustion characteristics associated with the one or more 3D models generated by the modeling component 104, and/or one or more other characteristics associated with the one or more 3D models generated by the modeling component 104. In an aspect, the machine learning component 106 can predict and/or model a flow network of a biological structure associated with the one or more 3D models, heat transfer throughout a biological structure associated with the one or more 3D models, combustion associated with a biological structure associated with the one or more 3D models, multiphase flow through a biological structure associated with the one or more 3D models and/or other characteristics of a biological structure associated with the one or more 3D models.

In an embodiment, the machine learning component 106 can predict the one or more characteristics associated with the one or more 3D models based on input data and one or more machine learning processes associated with the one or more 3D models. The input data can be, for example, a set of parameters for a fluid capable of flowing through the one or more 3D models, a set of parameters for a thermal energy capable of flowing through the one or more 3D models, a set of parameters for a combustion chemical reaction capable of flowing through the one or more 3D models, and/or another set of parameters for input provided to the one or more 3D models. In an embodiment, the input data can include one or more markers to facilitate identification of the input data. The one or more characteristics associated with the one or more 3D models can correspond to one or more characteristics of the biological structure. In one example, distinct types of control volumes (e.g., chambers) simulating reservoirs, volume mixing dynamics, volume inertial dynamics, volume pumping dynamics, and/or volume gravitational dynamics can be employed by the machine learning component 106 to model and/or simulate various fluid flow conditions associated with the one or more 3D models. In an aspect, the machine learning component 106 can also employ measured data and/or streamed data to set boundary conditions for one or more machine learning processes. For example, the machine learning component 106 can also employ measured data and/or streamed data to set boundary conditions for supply chambers and sink chambers and/or to establish driving forces for simulated physics phenomena (e.g., fluid dynamics, thermal dynamics, combustion dynamics, angular momentum, etc.).

The machine learning component 106 (e.g., one or more machine learning processes performed by the machine learning component 106) can also employ an automatic classification system and/or an automatic classification process to facilitate learning and/or generating inferences with respect to the one or more 3D models generated by the modeling component 104. For example, the machine learning component 106 (e.g., one or more machine learning processes performed by the machine learning component 106) can employ a probabilistic and/or statistical-based analysis (e.g., factoring into the analysis utilities and costs) to learn and/or generate inferences with respect to the one or more 3D models generated by the modeling component 104. The machine learning component 106 (e.g., one or more machine learning processes performed by the machine learning component 106) can employ, for example, a support vector machine (SVM) classifier to learn and/or generate inferences with respect to the one or more 3D models generated by the modeling component 104. Additionally or alternatively, the machine learning component 106 (e.g., one or more machine learning processes performed by the machine learning component 106) can employ other classification techniques associated with Bayesian networks, decision trees and/or probabilistic classification models. Classifiers employed by the machine learning component 106 (e.g., one or more machine learning processes performed by the machine learning component 106) can be explicitly trained (e.g., via a generic training data) as well as implicitly trained (e.g., via receiving extrinsic information). For example, with respect to SVM's that are well understood, SVM's are configured via a learning or training phase within a classifier constructor and feature selection module. A classifier is a function that maps an input attribute vector, x=(x1, x2, x3, x4, xn), to a confidence that the input belongs to a class—that is, f(x)=confidence (class).

In an aspect, the machine learning component 106 can include an inference component that can further enhance automated aspects of the machine learning component 106 utilizing in part inference based schemes to facilitate learning and/or generating inferences with respect to the one or more 3D models generated by the modeling component 104. The machine learning component 106 (e.g., one or more machine learning processes performed by the machine learning component 106) can employ any suitable machine-learning based techniques, statistical-based techniques and/or probabilistic-based techniques. For example, the machine learning component 106 (e.g., one or more machine learning processes performed by the machine learning component 106) can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the machine learning component 106 (e.g., one or more machine learning processes performed by the machine learning component 106) can perform a set of machine learning computations associated with the one or more 3D models generated by the modeling component 104. For example, the machine learning component 106 (e.g., one or more machine learning processes performed by the machine learning component 106) can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations.

In an embodiment, the modeling component 104 can integrate a first 3D model associated with a first biological structure and a second 3D model associated with a second biological structure to generate a 3D model for a biological structure. For example, a 3D model generated by the modeling component 104 can be a combination of two or more 3D models. In an aspect, first geometric features of the first 3D model can be combined with second geometric features of the second 3D model. The first geometric features of the first 3D model can include, for example, chambers, cavities, vessels, channels, and/or other geometric features of the first 3D model. Similarly, the second geometric features of the second 3D model can include, for example, chambers, cavities, vessels, channels, and/or other geometric features of the second 3D model. As such, chambers, cavities, vessels, channels, and/or other geometric features of the first 3D model and the second 3D model can be combined. In another embodiment, the first 3D model can comprise a first set of supply nodes and a first set of sink nodes that form a first flow network for characteristics of the first 3D model. For instance, fluid provided through the first 3D model can flow from a supply node to a sink node of the first 3D model. Additionally, the second 3D model can comprise a second set of supply nodes and a second set of sink nodes that form a second flow network for characteristics of the second 3D model. For instance, fluid provided through the second 3D model can flow from a supply node to a sink node of the second 3D model. The modeling component 104 can combine the first flow network of the first 3D model with the second flow network of the second 3D model. For example, the first set of supply nodes of the first 3D model can be combined with the second set of supply nodes of the second 3D model. Furthermore, the first set of sink nodes of the first 3D model can be combined with the second set of sink nodes of the second 3D model.

In another embodiment, the machine learning component 106 can perform a first machine learning process associated with the first 3D model and a second machine learning process associated with the second 3D model. For instance, the machine learning component 106 can perform learning (e.g., explicit learning and/or implicit learning) and/or can generate inferences with respect to the first 3D model via the first machine learning process. Furthermore, the machine learning component 106 can perform learning (e.g., explicit learning and/or implicit learning) and/or can generate inferences with respect to the second 3D model via the second machine learning process. The learning and/or generated inferences by the machine learning component 106 can facilitate determination of one or more characteristics associated with the one or more 3D models generated by the modeling component 104. Furthermore, the learning and/or generated inferences can be determined by the machine learning component 106 via one or more machine learning processes associated with the one or more 3D models. In an aspect, the machine learning component 106 can predict one or more characteristics of the biological structure based on the one or more first characteristics associated with the first 3D model and the one or more second characteristics associated with the second 3D model. In one example, the machine learning component 106 can predict the one or more characteristics of the biological structure based on the one or more first characteristics and the one or more second characteristics. The one or more first characteristics can include first fluid flow characteristics associated with the first 3D model, first thermal characteristics associated with the first 3D model, first combustion characteristics associated with the first 3D model and/or first physics behavior characteristics associated with the first 3D model. Furthermore, one or more second characteristics can include second fluid flow characteristics associated with the second 3D model, second thermal characteristics associated with the second 3D model, second combustion characteristics associated with the second 3D model and/or second physics behavior characteristics associated with the second 3D model. In an embodiment, the machine learning component 106 can facilitate interaction between the first 3D model and the second 3D model based on the input data associated with the machine learning component 106. For example, interaction of the one or more first characteristics associated with the first 3D model and the one or more second characteristics associated with the second 3D model can be determined by the machine learning component 106 based on the input data.

The 3D health assessment component 108 can provide a 3D health assessment environment associated with the 3D model. For instance, the 3D health assessment component 108 can provide a 3D health assessment environment associated with a biological structure and/or a 3D model generated by the modeling component 104. The 3D health assessment environment can be a single fluid system health assessment tool. For example, the 3D health assessment environment can be a tool that provides functionality of numerous tools with respect to fluid systems to provide multi-dimensional type analyses. In one example, the 3D health assessment environment can provide a flow integrated health assessment environment, a heat transfer health assessment environment and/or a combustion health assessment environment. The 3D health assessment environment associated with the 3D health assessment component 108 can be employed to apply one or more numerical schemes to create predictions for machine simulated conditions associated with a biological structure. Prediction can be displayed and analyzed on a visual representation of actual hardware using a post-processing module of a graphical user interface. In an aspect, the 3D health assessment environment associated with the 3D health assessment component 108 can generate simulation predictions by conserving governing conservation equations for mass, momentum, energy, angular momentum, and/or species utilizing numerical analysis schemes. In certain embodiments, the fluid model tool component 102 can be employed as a service. For example, the 3D model associated with the fluid model tool component 102 can be a generated computational model employed by the 3D health assessment environment.

In an embodiment, the 3D health assessment environment can render physics modeling data of the biological structure based on the input data and the one or more characteristics of the biological structure on the 3D model. The physics modeling data can be indicative of a visual representation of the fluid flow, the thermal characteristics, the combustion characteristics and/or the physics behavior with respect to the 3D model. The physics modeling data can also be rendered on the 3D model as one or more dynamic visual elements. In an aspect, the 3D health assessment component 108 can alter visual characteristics (e.g., color, size, hues, shading, etc.) of at least a portion of the physics modeling data based on the fluid flow, the thermal characteristics, the combustion characteristics and/or the physics behavior. For example, different degrees of fluid flow through the 3D model can be presented as different visual characteristics (e.g., colors, sizes, hues or shades, etc.), different degrees of thermal characteristics with respect to the 3D model can be presented as different visual characteristics (e.g., colors, sizes, hues or shades, etc.), different degrees of combustion characteristics with respect to the 3D model can be presented as different visual characteristics (e.g., colors, sizes, hues or shades, etc.), different degrees of physics behavior with respect to the 3D model can be presented as different visual characteristics (e.g., colors, sizes, hues or shades, etc.), etc. In another aspect, the 3D health assessment environment for the 3D model can allow a user to zoom into or out from the 3D model associated with the physics modeling data, rotate a view for the 3D model associated with the physics modeling data, etc. As such, a user can view, analyze and/or interact with the 3D model associated with the physics modeling data to facilitate determination of impact of a fluid flow, thermal characteristics, combustion characteristics and/or physics behavior with respect to a biological structure associated with the 3D model.

Figure 2:
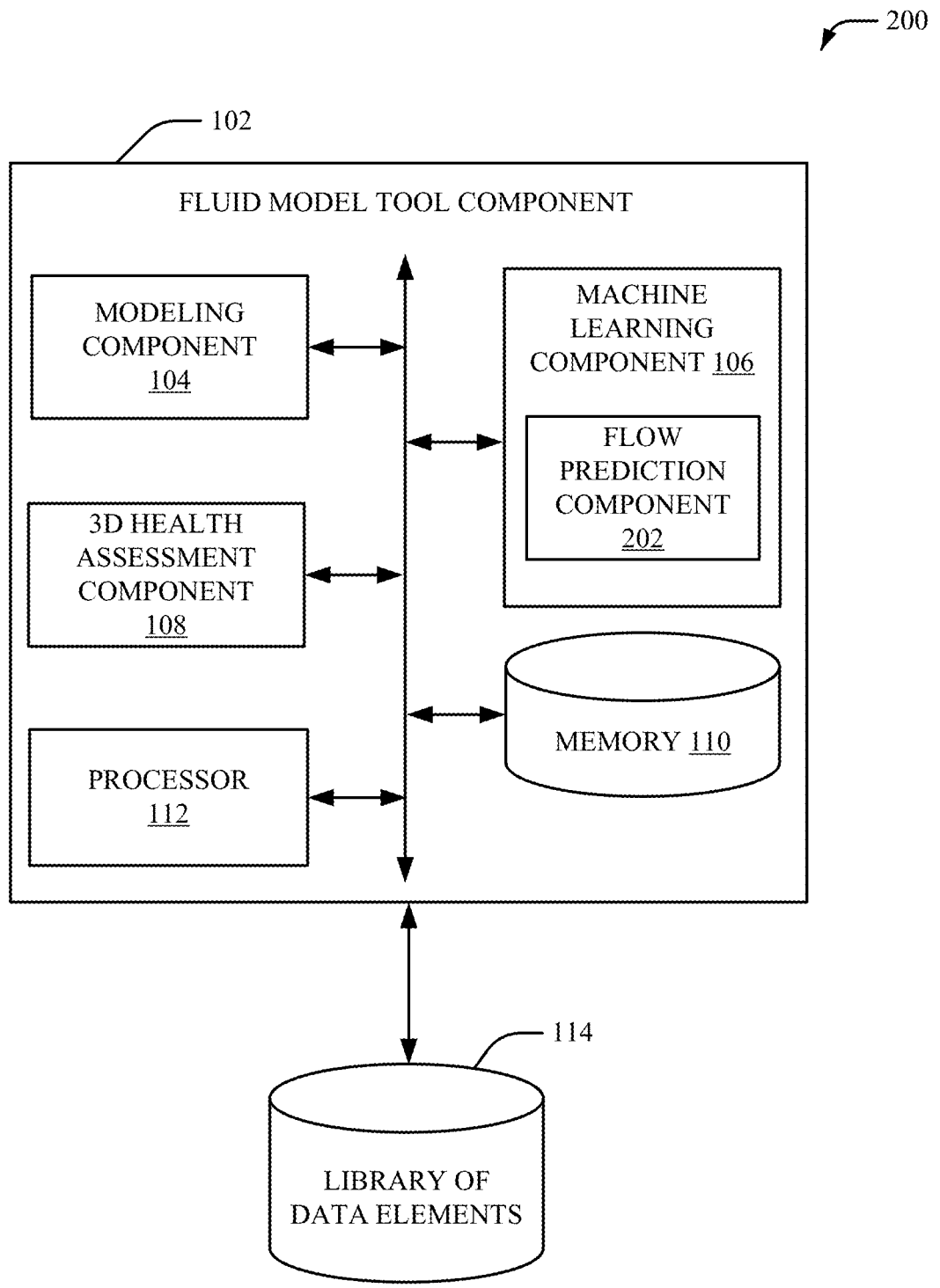
FIG. 2 illustrates a high-level block diagram of an example fluid model tool component associated with flow prediction, in accordance with various aspects and implementations described herein.

Referring now to FIG. 2, there is illustrated an example system 200 that provides a multiple fluid model tool for multi-dimensional fluid modeling of a biological structure, according to an aspect of the subject disclosure. Repetitive description of like elements employed in other embodiments described herein is omitted for sake of brevity.

The system 200 can include the fluid model tool component 102 and/or the multi-dimensional medical imaging data 114. The fluid model tool component 102 can include the modeling component 104, the machine learning component 106, the 3D health assessment component 108, the memory 110 and/or the processor 112. In the embodiment shown in FIG. 2, the machine learning component 106 can include a flow prediction component 202. The flow prediction component 202 can predict fluid flow and physics behavior associated with the 3D model. For instance, the flow prediction component 202 can perform a machine learning process associated with fluid flow through the 3D model. The flow prediction component 202 can perform the machine learning process based on input data indicative of input received by a biological structure associated with the 3D model. For example, the input data can include fluid data indicative of a fluid provided to a biological structure associated with the 3D model. The fluid data can include one or more properties of the fluid such as, for example, a fluid type of the fluid, a density of the fluid, a viscosity of the fluid, a volume of the fluid, a weight of the fluid, a temperature of the fluid and/or another property of the fluid. In an embodiment, the fluid data can include one or more markers (e.g., one or more chemical markers) in the fluid data to facilitate identification and/or monitoring of the fluid data with respect to the biological structure. The input data can by employed by the flow prediction component 202 to predict the fluid flow. The fluid flow can be, for example, fluid flow of the input data (e.g., the fluid) through the biological structure associated with the 3D model. The physics behavior can be physics behavior of the fluid flow. For instance, the physics behavior can be simulated physics and/or changes of the fluid flow. Furthermore, the physics behavior can be simulated fluid flow conditions associated with the 3D model. The physics behavior can also include correlations and/or behavior determined based on one or more mathematical equations associated with fluid flow such as, for example, conservation equations for mass associated with a fluid, conservation equations for momentum associated with a fluid, conservation equations for energy associated with a fluid, conservation equations for angular momentum associated with a fluid, and/or another mathematical equation associated with fluid flow.

Figure 3:
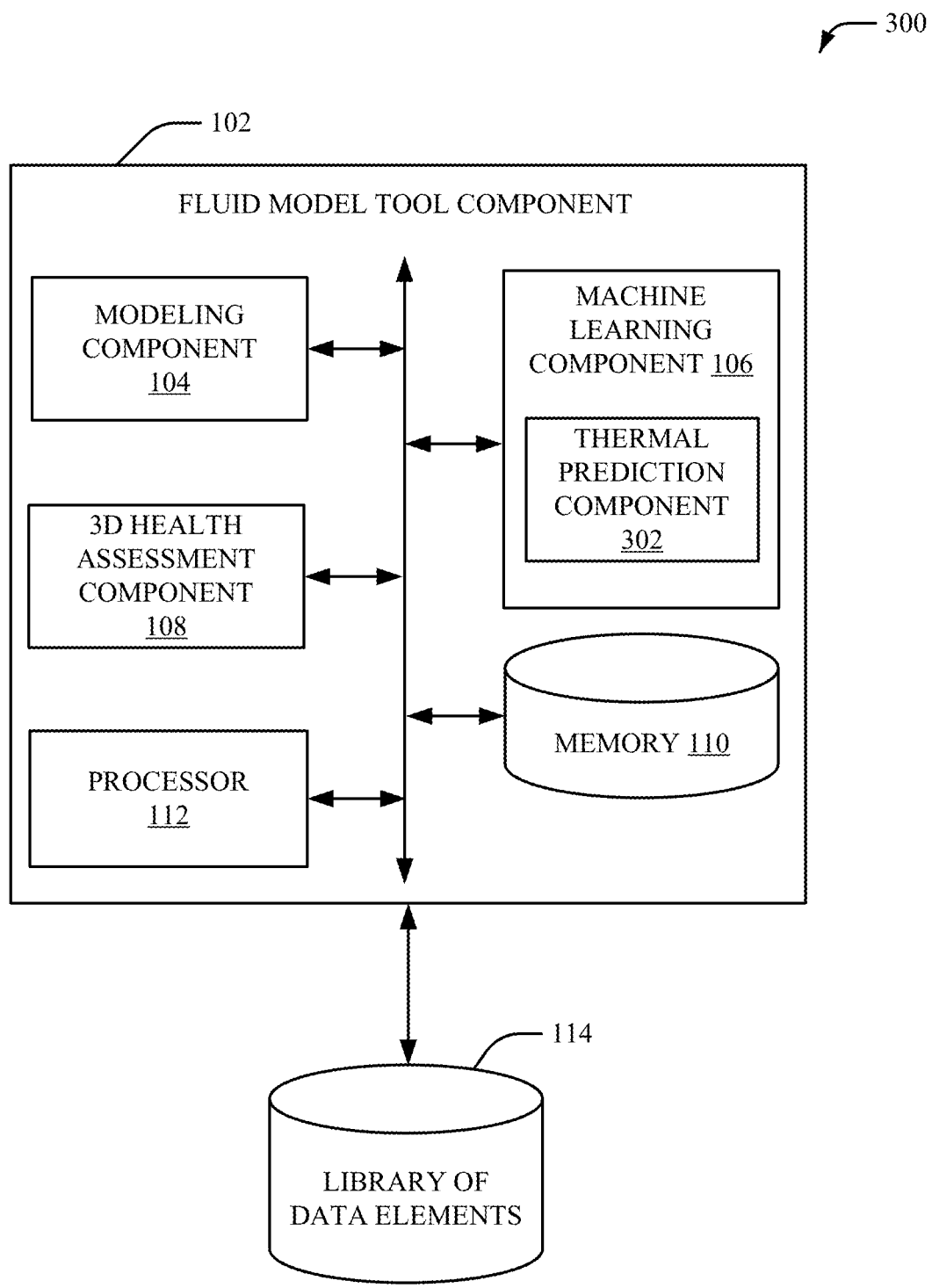
FIG. 3 illustrates a high-level block diagram of an example fluid model tool component associated with thermal prediction, in accordance with various aspects and implementations described herein.

Referring now to FIG. 3, there is illustrated an example system 300 that provides a multiple fluid model tool for multi-dimensional fluid modeling of a biological structure, according to an aspect of the subject disclosure. Repetitive description of like elements employed in other embodiments described herein is omitted for sake of brevity.

The system 300 can include the fluid model tool component 102 and/or the multi-dimensional medical imaging data 114. The fluid model tool component 102 can include the modeling component 104, the machine learning component 106, the 3D health assessment component 108, the memory 110 and/or the processor 112. In the embodiment shown in FIG. 3, the machine learning component 106 can include a thermal prediction component 302. In certain embodiments, the machine learning component 106 can include the thermal prediction component 302 and the flow prediction component 202. The thermal prediction component 302 can predict thermal characteristics and physics behavior associated with the 3D model. For instance, the thermal prediction component 302 can perform a machine learning process associated with thermal characteristics associated with the 3D model. The thermal prediction component 302 can perform the machine learning process based on input data indicative of input received by a biological structure associated with the 3D model. For example, the input data can include the fluid data indicative of a fluid provided to a biological structure associated with the 3D model. The input data can by employed by the thermal prediction component 302 to predict the thermal characteristics. The thermal characteristics can be, for example, a temperature associated with one or more regions of the 3D model, a heat capacity associated with one or more regions of the 3D model, thermal expansion associated with one or more regions of the 3D model, thermal conductivity associated with one or more regions of the 3D model, thermal stress associated with one or more regions of the 3D model, and/or another thermal characteristics associated with one or more regions of the 3D model. The physics behavior can be physics behavior of the thermal characteristics. For instance, the physics behavior can be simulated physics and/or changes of the thermal characteristics. Furthermore, the physics behavior can be simulated thermal conditions associated with the 3D model. The physics behavior can also include correlations and/or behavior determined based on one or more mathematical equations associated with thermal characteristics such as, for example, conservation equations for mass associated with thermal characteristics, conservation equations for momentum associated with thermal characteristics, conservation equations for energy associated with thermal characteristics, conservation equations for angular momentum associated with thermal characteristics, and/or another mathematical equation associated with thermal characteristics.

Figure 4:
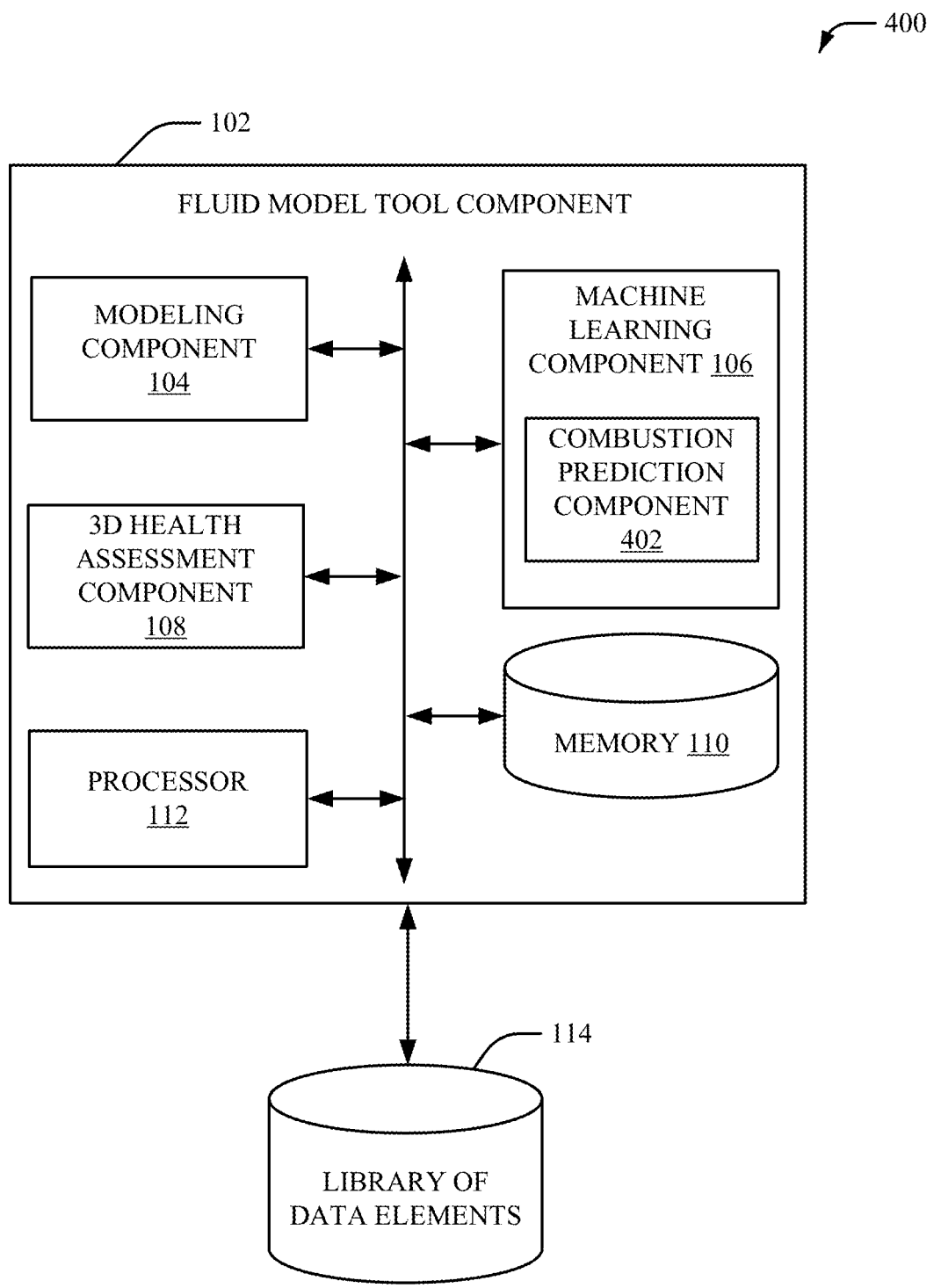
FIG. 4 illustrates a high-level block diagram of an example fluid model tool component associated with combustion prediction, in accordance with various aspects and implementations described herein.

Referring now to FIG. 4, there is illustrated an example system 400 that provides a multiple fluid model tool for multi-dimensional fluid modeling of a biological structure, according to an aspect of the subject disclosure. Repetitive description of like elements employed in other embodiments described herein is omitted for sake of brevity.

The system 400 can include the fluid model tool component 102 and/or the multi-dimensional medical imaging data 114. The fluid model tool component 102 can include the modeling component 104, the machine learning component 106, the 3D health assessment component 108, the memory 110 and/or the processor 112. In the embodiment shown in FIG. 4, the machine learning component 106 can include a combustion prediction component 402. In certain embodiments, in addition to the combustion prediction component 402, the machine learning component 106 can include the flow prediction component 202 and/or the thermal prediction component 302. The combustion prediction component 402 can predict combustion characteristics and physics behavior associated with the 3D model. For instance, the combustion prediction component 402 can perform a machine learning process associated with combustion characteristics associated with the 3D model. The combustion prediction component 402 can perform the machine learning process based on input data indicative of input received by a biological structure associated with the 3D model. For example, the input data can include the fluid data indicative of a fluid provided to a biological structure associated with the 3D model. Additionally or alternatively, the input data can include chemical data indicative of a chemical element provided to a biological structure associated with the 3D model. The input data can by employed by the combustion prediction component 402 to predict the combustion characteristics. The combustion characteristics can be, for example, information related to a chemical reaction associated with one or more regions of the 3D model such as, for example, a temperature measurement, a heating value, an elemental composition, a moisture content, a density, an acoustic measurement and/or another combustion characteristic associated with one or more regions of the 3D model. The physics behavior can be physics behavior of the combustion characteristics. For instance, the physics behavior can be simulated physics and/or changes of the combustion characteristics. Furthermore, the physics behavior can be simulated combustion conditions associated with the 3D model. The physics behavior can also include correlations and/or behavior determined based on one or more mathematical equations associated with combustion characteristics such as, for example, conservation equations for mass associated with combustion characteristics, conservation equations for momentum associated with combustion characteristics, conservation equations for energy associated with combustion characteristics, conservation equations for angular momentum associated with combustion characteristics, and/or another mathematical equation associated with combustion characteristics.

Figure 5:
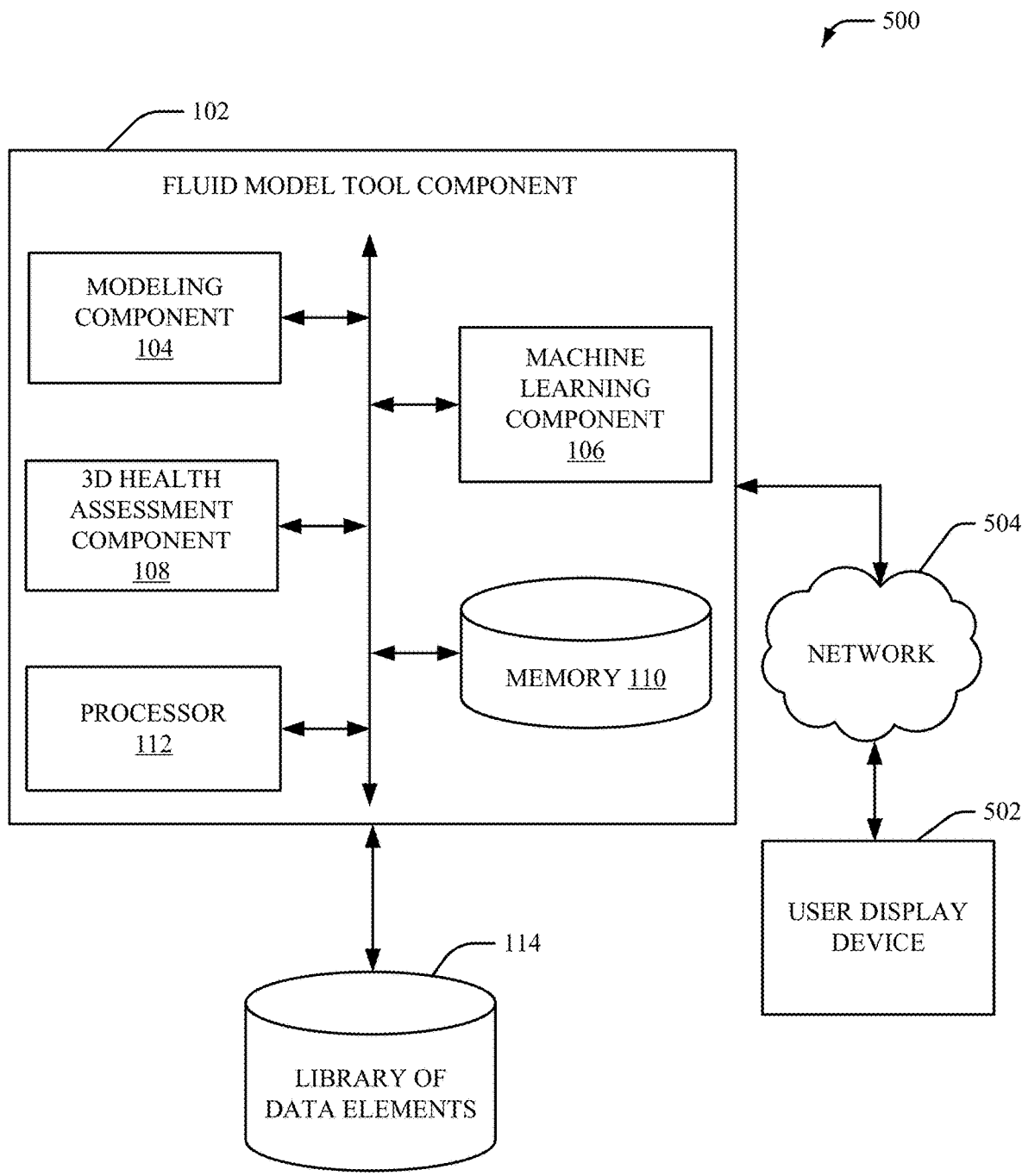
FIG. 5 illustrates a high-level block diagram of an example fluid model tool component in communication with a user display device, in accordance with various aspects and implementations described herein.

Referring now to FIG. 5, there is illustrated an example system 500 that provides a multiple fluid model tool for multi-dimensional fluid modeling of a biological structure, according to an aspect of the subject disclosure. Repetitive description of like elements employed in other embodiments described herein is omitted for sake of brevity.

The system 500 can include the fluid model tool component 102, the multi-dimensional medical imaging data 114 and a user display device 502. The user display device 502 can be in communication with the fluid model tool component 102 via a network 504. The network 504 can be a wired network and/or a wireless network. The fluid model tool component 102 can include the modeling component 104, the machine learning component 106, the 3D health assessment component 108, the memory 110 and/or the processor 112. In certain embodiments, the machine learning component 106 can include the flow prediction component 202, the thermal prediction component 302 and/or the combustion prediction component 402. The user display device 502 can display a 3D model and/or a 3D health assessment environment generated by the fluid model tool component 102. For example, a 3D model associated with the physics modeling data can be rendered on a graphical user interface associated with a display of the user display device 502. The user display device 502 can be a biological structure with a display such as, but not limited to, a computing biological structure, a computer, a desktop computer, a laptop computer, a monitor biological structure, a smart biological structure, a smart phone, a mobile biological structure, a handheld biological structure, a tablet, a portable computing biological structure or another type of user biological structure associated with a display.

Figure 6:
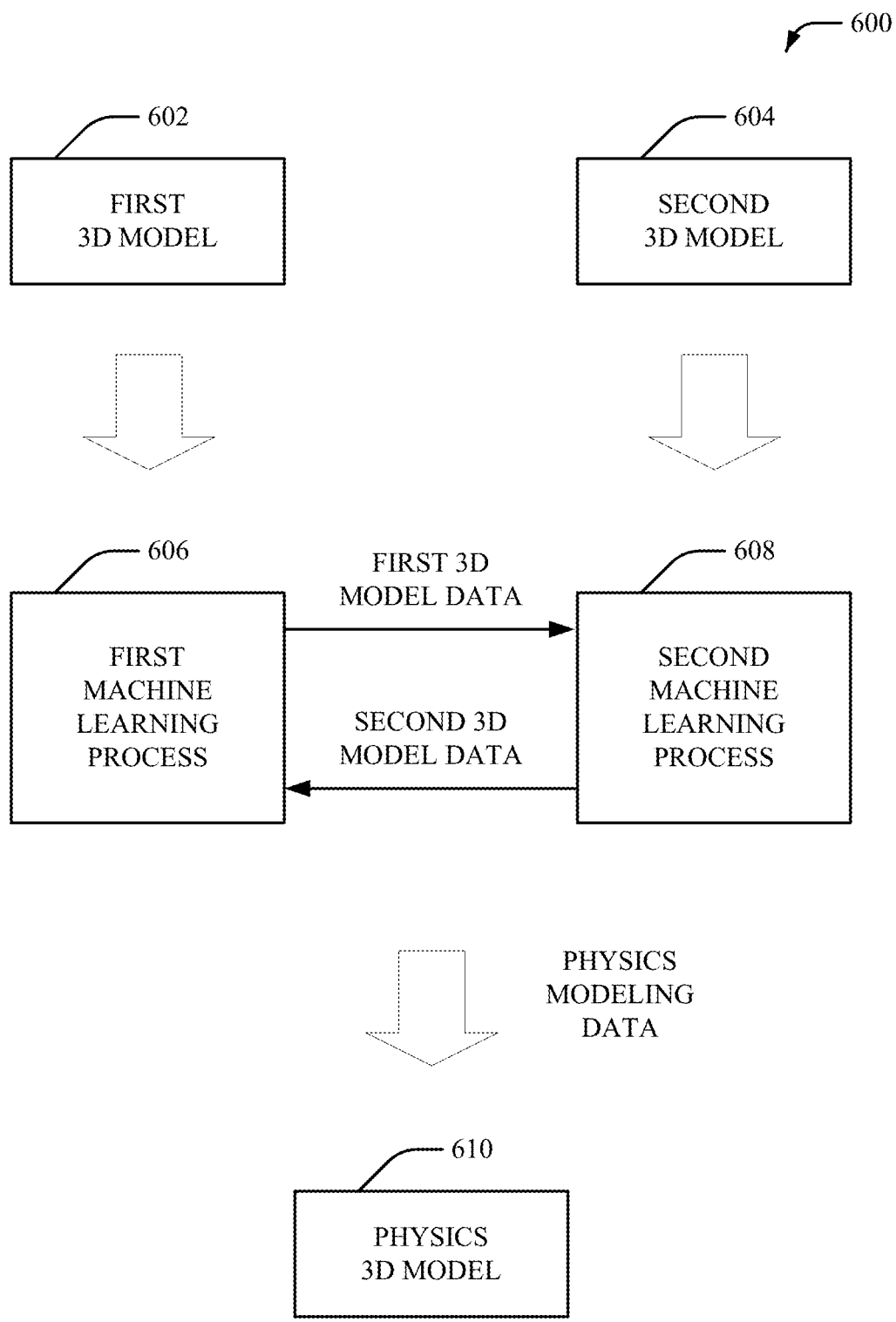
FIG. 6 illustrates an example system that provides multi-dimensional fluid modeling of a biological structure, in accordance with various aspects and implementations described herein.

Referring now to FIG. 6, there is illustrated an example system 600 that provides multi-dimensional fluid modeling of a biological structure, according to an aspect of the subject disclosure. Repetitive description of like elements employed in other embodiments described herein is omitted for sake of brevity.

The system 600 can include a first 3D model 602 and a second 3D model 604. The first 3D model 602 and the second 3D model 604 can be generated by the modeling component 104. In an aspect, the first 3D model 602 can be associated with a first biological structure and the second 3D model 604 can be associated with a second biological structure. In certain embodiments, the first 3D model 602 and/or the second 3D model 604 can be generated based on the multi-dimensional medical imaging data 114.

The system 600 can also include a first machine learning process 606 and a second machine learning process 608. The first machine learning process 606 and the second machine learning process 608 can be performed by the machine learning component 106. Furthermore, the first machine learning process 606 can be a machine learning process associated with the first 3D model 602 and the second machine learning process 608 can be a machine learning process associated with the second 3D model 604. In an aspect, the machine learning component 106 can perform the second machine learning process 608 based on first 3D model data (e.g., FIRST 3D MODEL DATA shown in FIG. 6) provided by the first machine learning process 606. The first 3D model data can be associated with the first 3D model 602. In one example, the first 3D model data can be generated during the first machine learning process 606. The first 3D model data can also include information related to learning and/or generated inferences associated with the first 3D model 602. Additionally or alternatively, the machine learning component 106 can perform the first machine learning process 606 based on second 3D model data (e.g., SECOND 3D MODEL DATA shown in FIG. 6) provided by the second machine learning process 608. The second 3D model data can be associated with the second 3D model 604. In one example, the second 3D model data can be generated during the second machine learning process 608. The second 3D model data can also include information related to learning and/or generated inferences associated with the second 3D model 604. In an embodiment, the modeling component 104 can integrate the first 3D model 602 and the second 3D model 604 prior to the first machine learning process 606 and/or the second machine learning process 608 to generate a 3D model of a biological structure. In another embodiment, the modeling component 104 can integrate the first 3D model 602 and the second 3D model 604 during the first machine learning process 606 and/or the second machine learning process 608 to generate a 3D model of a biological structure. In yet another embodiment, the modeling component 104 can integrate the first 3D model 602 and the second 3D model 604 after the first machine learning process 606 and/or the second machine learning process 608 to generate a 3D model of a biological structure.

Additionally, the system 600 can include a physics 3D model 610. The physics 3D model 610 can be associated with the first 3D model 602 and the second 3D model 604. For instance, the physics 3D model 610 can be associated with the 3D model generated by integrating the first 3D model 602 and the second 3D model 604. The physics 3D model 610 can also include physics modeling data (e.g., PHYSICS MODELING DATA shown in FIG. 6) generated by the first machine learning process 606 and the second machine learning process 608. The physics modeling data can be indicative of information associated with fluid dynamics, thermal dynamic and/or combustion dynamics. For instance, the physics modeling data can be rendered on the physics 3D model 610 to represent fluid flow, thermal characteristics, combustion characteristics and/or physics behavior for a biological structure associated with the physics 3D model 610. In one example, the physics modeling data can simulate physical phenomena such as, but not limited to, compressible fluid flow, incompressible fluid flow, buoyancy driven flow, rotating cavity system flow, conduction heat transfer, convection heat transfer, radiation heat transfer, combustion equilibrium-chemistry, species transport, and/or other physics behavior.

Figure 7:
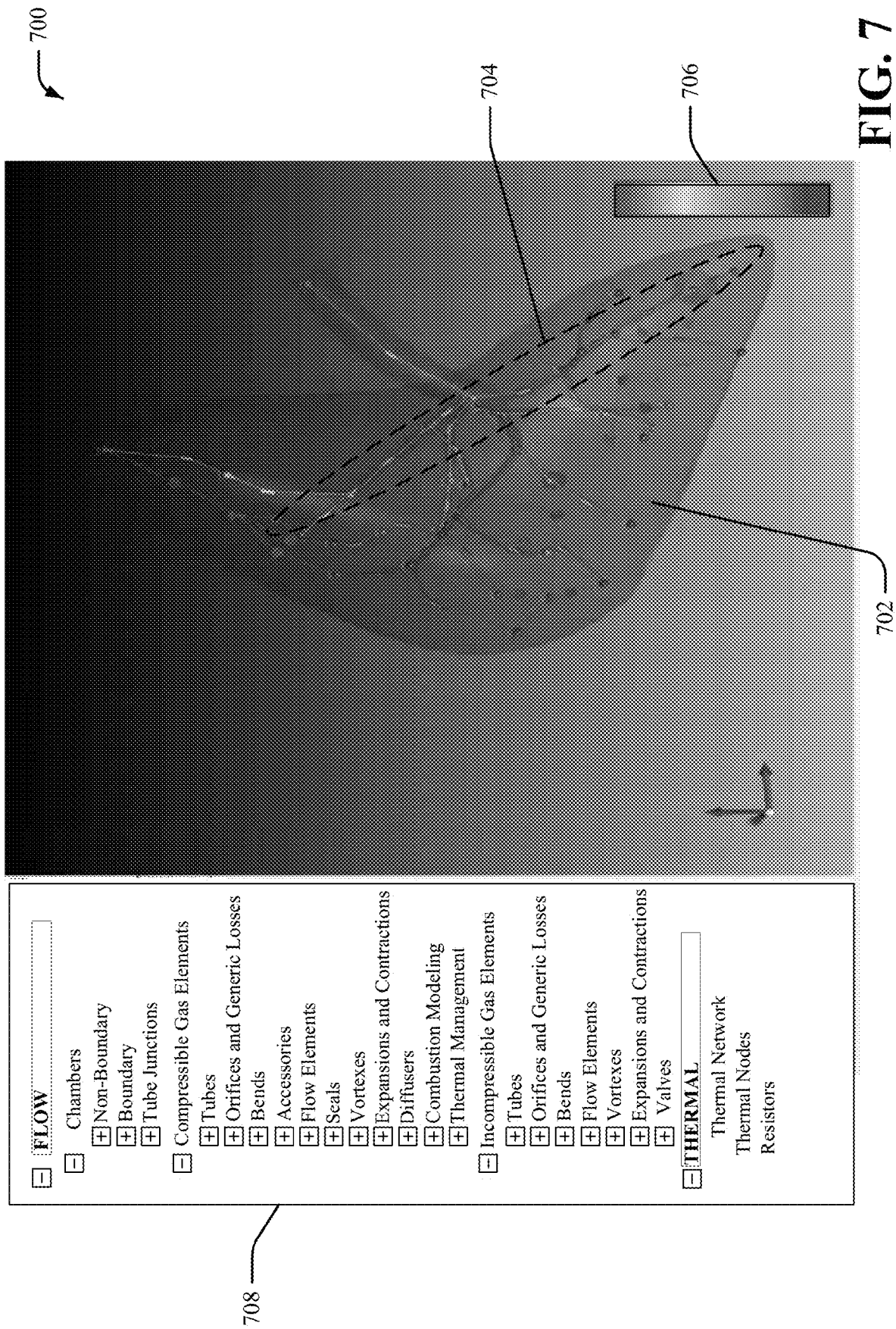
FIG. 7 illustrates an example 3D model, in accordance with various aspects and implementations described herein.

FIG. 7 illustrates an example 3D model 700, in accordance with various aspects and implementations described herein. The 3D model 700 can, for example, correspond to the physics 3D model 610 and/or a 3D model generated by the fluid model tool component 102. The 3D model 700 can illustrate fluid dynamics, thermal dynamic and/or combustion dynamics with respect to health assessment of a biological structure. For example, the 3D model 700 can be a 3D model where physics modeling data associated with fluid dynamics, thermal dynamic and/or combustion dynamics is rendered on a biological structure. In an aspect, the 3D model 700 can include a biological structure portion 702 of the 3D model 700 and physics modeling data 704 that is rendered on the biological structure portion 702. Visual characteristics (e.g., a color, a size, a hues, shading, etc.) of the physics modeling data 704 can be dynamic based on a value of the physics modeling data 704. For instance, a first portion of the physics modeling data 704 associated with first physics modeling information can comprise a first visual characteristics and a second portion of the physics modeling data 704 associated with second physics modeling information can comprise a second visual characteristic. In an embodiment, the physics modeling data 704 can be determined by the machine learning component 106. In one example, the physics modeling data 704 can be associated with a set of control volumes and/or a flow network related to fluid dynamics, thermal dynamic and/or combustion dynamics.

In another example, the physics modeling data 704 can be associated with blood tracking for the biological structure portion 702 of the 3D model 700, waste tracking for the biological structure portion 702 of the 3D model 700, laminar and transitional regimes for the biological structure portion 702 of the 3D model 700, non-Newtonian friction losses for the biological structure portion 702 of the 3D model 700, elastic-wall tube structures for the biological structure portion 702 of the 3D model 700, fluid-structure interactions for the biological structure portion 702 of the 3D model 700, feedback data for the biological structure portion 702 of the 3D model 700, etc. In an embodiment, a 3D health assessment environment associated with the 3D model 700 can include a heat bar 706. The heat bar 706 can include a set of colors that correspond to different values for the physics modeling data 704. For example, a first color (e.g., a color red) in the heat bar 706 can correspond to a first value for the physics modeling data 704 and a second color (e.g., a color blue) in the heat bar 706 can correspond to a second value for the physics modeling data 704. In another embodiment, a 3D health assessment environment associated with the 3D model 700 can include a side bar 708. The side bar 708 can include information to facilitate generation of the 3D model 700 and/or the physics modeling data 704. For example, the side bar 708 can facilitate selection of a type of physics modeling data (e.g., flow dynamics, thermal dynamics, combustion dynamics, etc.) provided by the physics modeling data 704.

The aforementioned systems and/or biological structures have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

FIGS. 8-12 illustrate methodologies and/or flow diagrams in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable biological structure or storage media.

Figure 8:
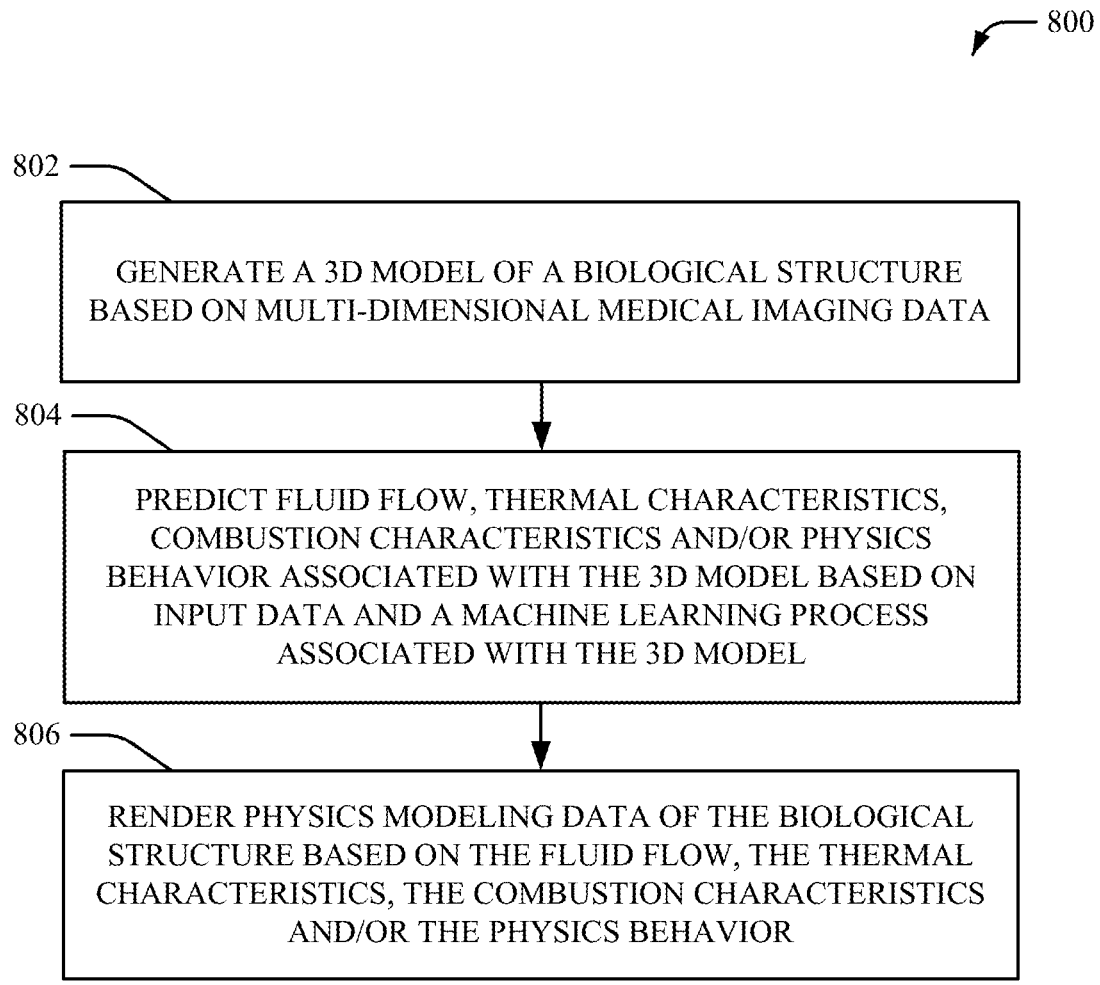
FIG. 8 depicts a flow diagram of an example method for providing multi-dimensional fluid modeling of a biological structure, in accordance with various aspects and implementations described herein.

Referring to FIG. 8, there illustrated is a methodology 800 for providing multi-dimensional fluid modeling of a biological structure, according to an aspect of the subject innovation. As an example, the methodology 800 can be utilized in various applications, such as, but not limited to, modeling systems, biological structure systems, cloud-based systems, medical systems, diagnostics systems, prognostics systems, medical biological structure systems, medical imaging systems, medical modeling systems, health assessment systems, simulation systems, enterprise systems, enterprise imaging solution systems, medical testing systems, advanced medical tool systems, artificial intelligence systems, machine learning systems, neural network systems, etc. At 802, a 3D model of a biological structure is generated (e.g., by modeling component 104) based on multi-dimensional medical imaging data. The multi-dimensional medical imaging data can be, for example, 3D medical imaging data associated with one or more medical imaging biological structures. For instance, the multi-dimensional medical imaging data can be a set of consecutive images and/or a set of data that is repeatedly captured via a set of sensors (e.g., a set of sensors associated with a medical imaging biological structure) during an interval of time. The multi-dimensional medical imaging data can be received directly from one or more medical imaging biological structures. Alternatively, the multi-dimensional medical imaging data can be stored in one or more databases that receives and/or stores the multi-dimensional medical imaging data associated with the one or more medical imaging biological structures. A medical imaging biological structure can be, for example, a CT biological structure, a MRI biological structure, a PET biological structure, a CAT biological structure, an ultrasound biological structure, another type of medical imaging biological structure, etc. In an aspect, the multi-dimensional medical imaging data can be rendered from one or more 2D images. For example, the multi-dimensional medical imaging data can be rendered into 3D medical imaging data from 2D medical imaging data (e.g., 2D CT imaging data, 2D MRI imaging data, etc.). Additionally or alternatively, the multi-dimensional medical imaging data can be generated based on one or more 3D sensor associated with one or more 3D imaging biological structures. In an embodiment, the generating the 3D model can include integrating a first 3D model associated with a first biological structure and a second 3D model associated with a second biological structure.

At 804, fluid flow, thermal characteristics, combustion characteristics and/or physics behavior associated with the 3D model are predicted (e.g., by machine learning component 106) based on input data and a machine learning process associated with the 3D model. For instance, the machine learning process can perform learning and/or can generate inferences with respect to fluid flow, thermal characteristics, combustion characteristics and/or physics behavior associated with the 3D model. The input data can include fluid data and/or chemical data associated with an input provided to a biological structure associated with the 3D model. The physics behavior can be indicative of behavior related to fluid dynamics, thermal dynamics and/or combustion dynamics throughout the biological structure associated with the 3D model in response to the input data. In an embodiment, the predicting can include performing a first machine learning process associated with the first 3D model and performing a second machine learning process associated with the second 3D model.

At 806, physics modeling data of the biological structure is rendered (e.g., by 3D health assessment component 108) based on the fluid flow, the thermal characteristics, the combustion characteristics and/or the physics behavior. For example, the physics modeling data can be indicative of a visual representation of the fluid flow, the thermal characteristics, the combustion characteristics and/or the physics behavior with respect to the 3D model. The physics modeling data can be rendered on the 3D model as dynamic visual elements. In an embodiment, the rendering of the physics modeling data can include providing a 3D health assessment environment associated with the 3D model.

Figure 9:
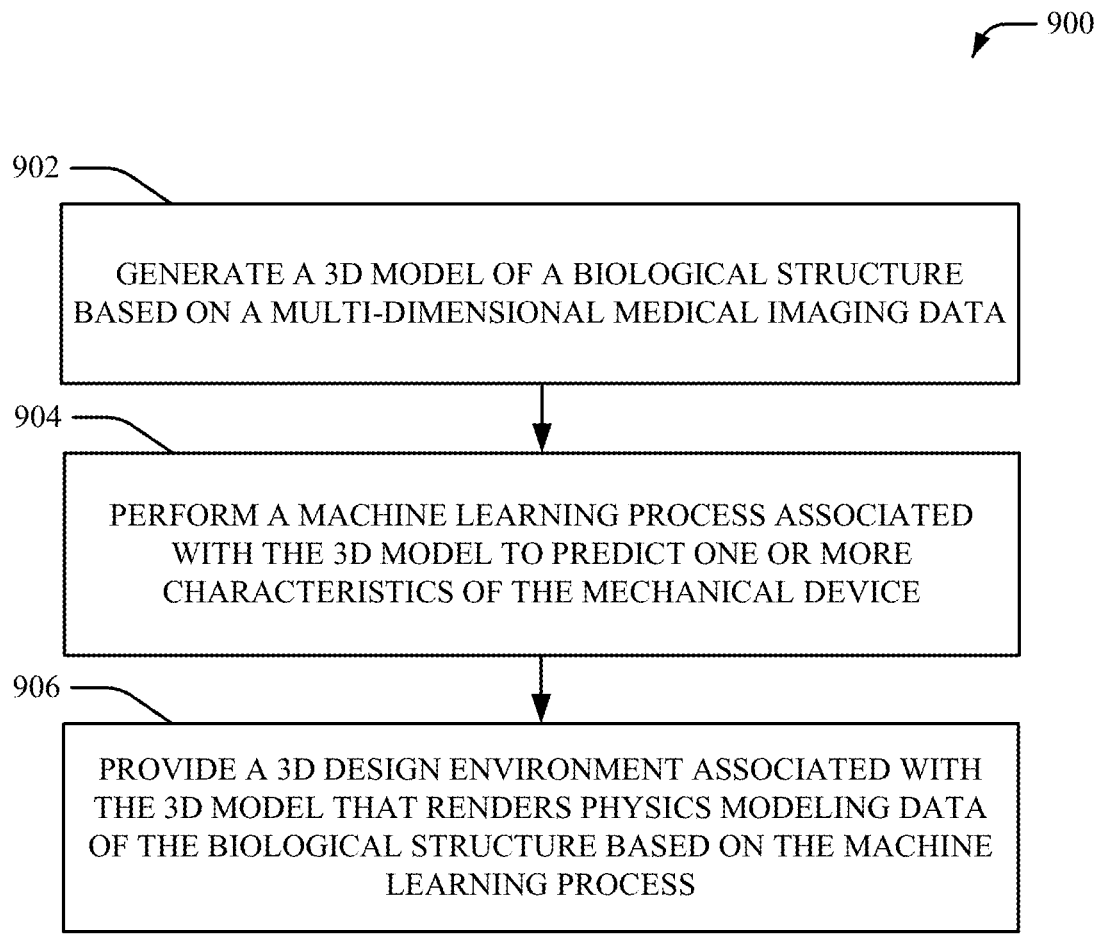
FIG. 9 depicts a flow diagram of another example method for providing multi-dimensional fluid modeling of a biological structure, in accordance with various aspects and implementations described herein.

Referring to FIG. 9, there illustrated is a methodology 900 for providing multi-dimensional fluid modeling of a biological structure, according to another aspect of the subject innovation. As an example, the methodology 900 can be utilized in various applications, such as, but not limited to, modeling systems, biological structure systems, cloud-based systems, medical systems, diagnostics systems, prognostics systems, medical biological structure systems, medical imaging systems, medical modeling systems, health assessment systems, simulation systems, enterprise systems, enterprise imaging solution systems, medical testing systems, advanced medical tool systems, artificial intelligence systems, machine learning systems, neural network systems, etc. At 902, a 3D model of a biological structure is generated (e.g., by modeling component 104) based on multi-dimensional medical imaging data. The multi-dimensional medical imaging data can be, for example, 3D medical imaging data associated with one or more medical imaging biological structures. For instance, the multi-dimensional medical imaging data can be a set of consecutive images and/or a set of data that is repeatedly captured via a set of sensors (e.g., a set of sensors associated with a medical imaging biological structure) during an interval of time. The multi-dimensional medical imaging data can be received directly from one or more medical imaging biological structures. Alternatively, the multi-dimensional medical imaging data can be stored in one or more databases that receives and/or stores the multi-dimensional medical imaging data associated with the one or more medical imaging biological structures. A medical imaging biological structure can be, for example, a CT biological structure, a MRI biological structure, a PET biological structure, a CAT biological structure, an ultrasound biological structure, another type of medical imaging biological structure, etc. In an aspect, the multi-dimensional medical imaging data can be rendered from one or more 2D images. For example, the multi-dimensional medical imaging data can be rendered into 3D medical imaging data from 2D medical imaging data (e.g., 2D CT imaging data, 2D MRI imaging data, etc.). Additionally or alternatively, the multi-dimensional medical imaging data can be generated based on one or more 3D sensor associated with one or more 3D imaging biological structures. In an embodiment, the generating the 3D model can include integrating a first 3D model associated with a first biological structure and a second 3D model associated with a second biological structure.

At 904, a machine learning process associated with the 3D model is performed (e.g., by machine learning component 106) to predict one or more characteristics of the biological structure. The machine learning process can perform learning and and/or can generate inferences to predict the one or more characteristics of the biological structure. The one or more characteristics can be related to fluid dynamics, thermal dynamics and/or combustion dynamics throughout the biological structure associated with the 3D model. For instance, the one or more characteristics can include fluid flow characteristics, thermal characteristics, combustion characteristics and/or physics behavior characteristics.

At 906, a 3D health assessment environment associated with the 3D model that renders physics modeling data of the biological structure is provided (e.g., by 3D health assessment component 108) based on the machine learning process. The 3D health assessment environment can apply one or more numerical schemes associated with the machine learning process to create predictions for machine simulated conditions for the 3D model. Predictions associated with the machine learning process can be displayed and/or analyzed on a visual representation of the biological structure using post-processing associated with a graphical user interface. In an aspect, the 3D health assessment environment can generate simulation predictions for the one or more characteristics can be related to fluid dynamics, thermal dynamics and/or combustion dynamics throughout the biological structure associated with the 3D model. For instance, the 3D health assessment environment can generate simulation predictions for fluid flow characteristics, thermal characteristics, combustion characteristics and/or physics behavior characteristics of the biological structure associated with the 3D model.

Figure 10:
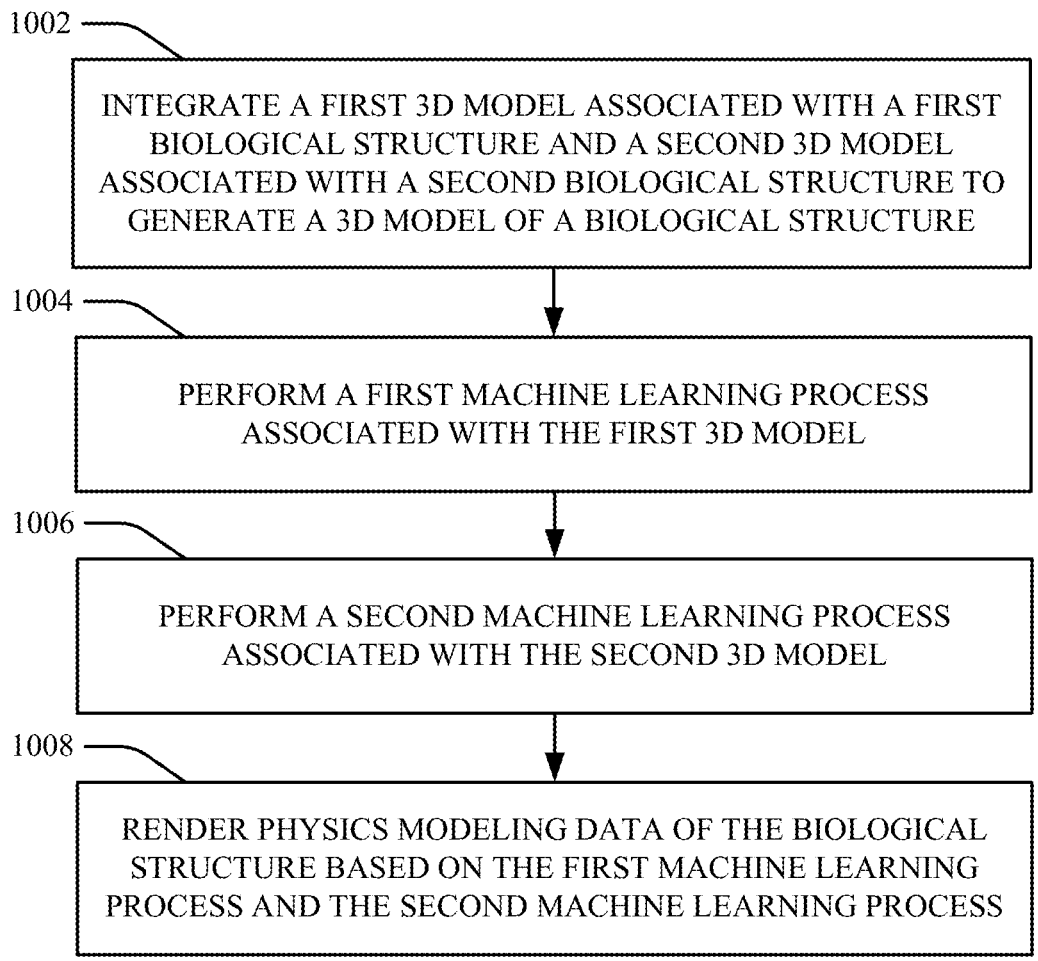
FIG. 10 depicts a flow diagram of yet another example method for providing multi-dimensional fluid modeling of a biological structure, in accordance with various aspects and implementations described herein.

Referring to FIG. 10, there illustrated is a methodology 1000 for providing multi-dimensional fluid modeling of a biological structure, according to yet another aspect of the subject innovation. As an example, the methodology 1000 can be utilized in various applications, such as, but not limited to, modeling systems, biological structure systems, cloud-based systems, medical systems, diagnostics systems, prognostics systems, medical biological structure systems, medical imaging systems, medical modeling systems, health assessment systems, simulation systems, enterprise systems, enterprise imaging solution systems, medical testing systems, advanced medical tool systems, artificial intelligence systems, machine learning systems, neural network systems, etc. At 1002, a first 3D model associated with a first biological structure and a second 3D model associated with a second biological structure are integrated (e.g., by modeling component 104) to generate a 3D model of a biological structure. For example, a first set of data elements associated with the first 3D model can be combined with a second set of data elements associated with the second 3D model. In another example, multi-dimensional medical imaging data associated with the first 3D model can be combined with second multi-dimensional medical imaging associated with the second 3D model.

At 1004, a first machine learning process associated with the first 3D model is performed (e.g., by machine learning component 106). The first machine learning process can perform learning and and/or can generate inferences to predict one or more characteristics of the first biological structure. The one or more characteristics of the first biological structure can be related to fluid dynamics, thermal dynamics and/or combustion dynamics throughout the first biological structure associated with the first 3D model. For instance, the one or more characteristics of the first biological structure can include fluid flow characteristics, thermal characteristics, combustion characteristics and/or physics behavior characteristics.

At 1006, a second machine learning process associated with the second 3D model is performed (e.g., by machine learning component 106). The second machine learning process can perform learning and and/or can generate inferences to predict one or more characteristics of the second biological structure. The one or more characteristics of the second biological structure can be related to fluid dynamics, thermal dynamics and/or combustion dynamics throughout the second biological structure associated with the second 3D model. For instance, the one or more characteristics of the second biological structure can include fluid flow characteristics, thermal characteristics, combustion characteristics and/or physics behavior characteristics.

At 1008, physics modeling data of the biological structure is rendered (e.g., by 3D health assessment component 108) based on the first machine learning process and the second machine learning process. The physics modeling data can be indicative of information associated with fluid dynamics, thermal dynamic and/or combustion dynamics determined and/or predicted by the first machine learning process and the second machine learning process. For instance, the physics modeling data can be rendered on the 3D model to represent fluid flow, thermal characteristics, combustion characteristics and/or physics behavior for the biological structure associated with the 3D model.

Figure 11:
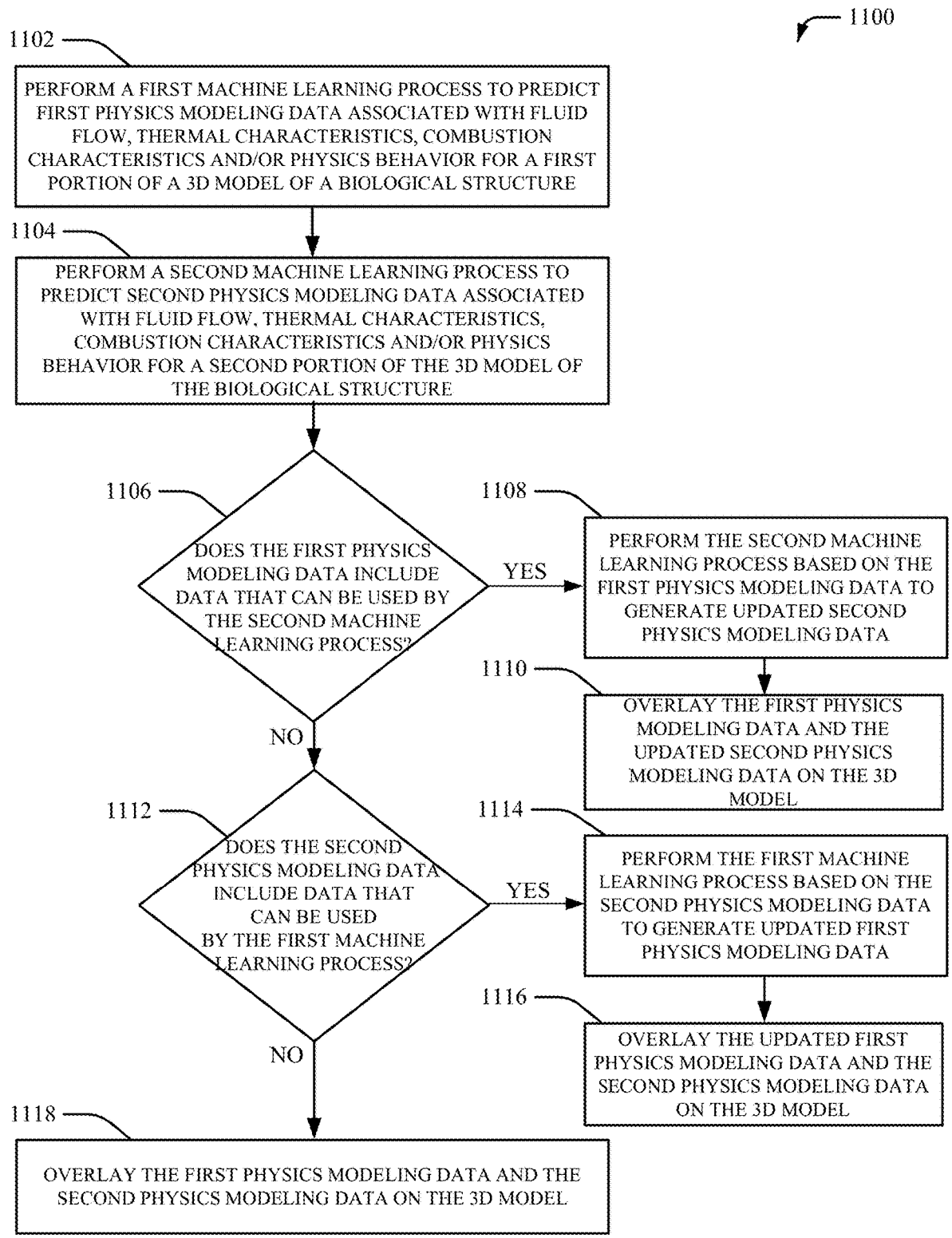
FIG. 11 depicts a flow diagram of yet another example method for providing multi-dimensional fluid modeling of a biological structure, in accordance with various aspects and implementations described herein.

Referring to FIG. 11, there illustrated is a methodology 1100 for providing multi-dimensional fluid modeling of a biological structure, according to yet another aspect of the subject innovation. As an example, the methodology 1100 can be utilized in various applications, such as, but not limited to, modeling systems, biological structure systems, cloud-based systems, medical systems, diagnostics systems, prognostics systems, medical biological structure systems, medical imaging systems, medical modeling systems, health assessment systems, simulation systems, enterprise systems, enterprise imaging solution systems, medical testing systems, advanced medical tool systems, artificial intelligence systems, machine learning systems, neural network systems, etc. At 1102, a first machine learning process is performed (e.g., by machine learning component 106) to predict first physics modeling data associated with fluid flow, thermal characteristics, combustion characteristics and/or physics behavior for a first portion of a 3D model of a biological structure. At 1104, a second machine learning process is performed (e.g., by machine learning component 106) to predict second physics modeling data associated with fluid flow, thermal characteristics, combustion characteristics and/or physics behavior for a second portion of the 3D model of the biological structure.

At 1106, it is determined (e.g., by machine learning component 106) whether the first physics modeling data includes data that can be used by the second machine learning process. If yes, the methodology 1100 proceeds to 1108. If no, the methodology 1100 proceeds to 1112. At 1108, the second machine learning process is performed (e.g., by machine learning component 106) based on the first physics modeling data to generate updated second physics modeling data. Then, the methodology 1100 proceeds to 1110. At 1110, the first physics modeling data and the updated second physics modeling data are overlaid (e.g., by 3D health assessment component 108) on the 3D model.

At 1112, it is determined (e.g., by machine learning component 106) whether the second physics modeling data includes data that can be used by the first machine learning process. If yes, the methodology 1100 proceeds to 1114. If no, the methodology 1100 proceeds to 1118. At 1114, the first machine learning process is performed (e.g., by machine learning component 106) based on the second physics modeling data to generate updated first physics modeling data. Then, the methodology 1100 proceeds to 1116. At 1116, the updated first physics modeling data and the second physics modeling data are overlaid (e.g., by 3D health assessment component 108) on the 3D model. At 1118, the first physics modeling data and the second physics modeling data are overlaid (e.g., by 3D health assessment component 108) on the 3D model.

Figure 12:
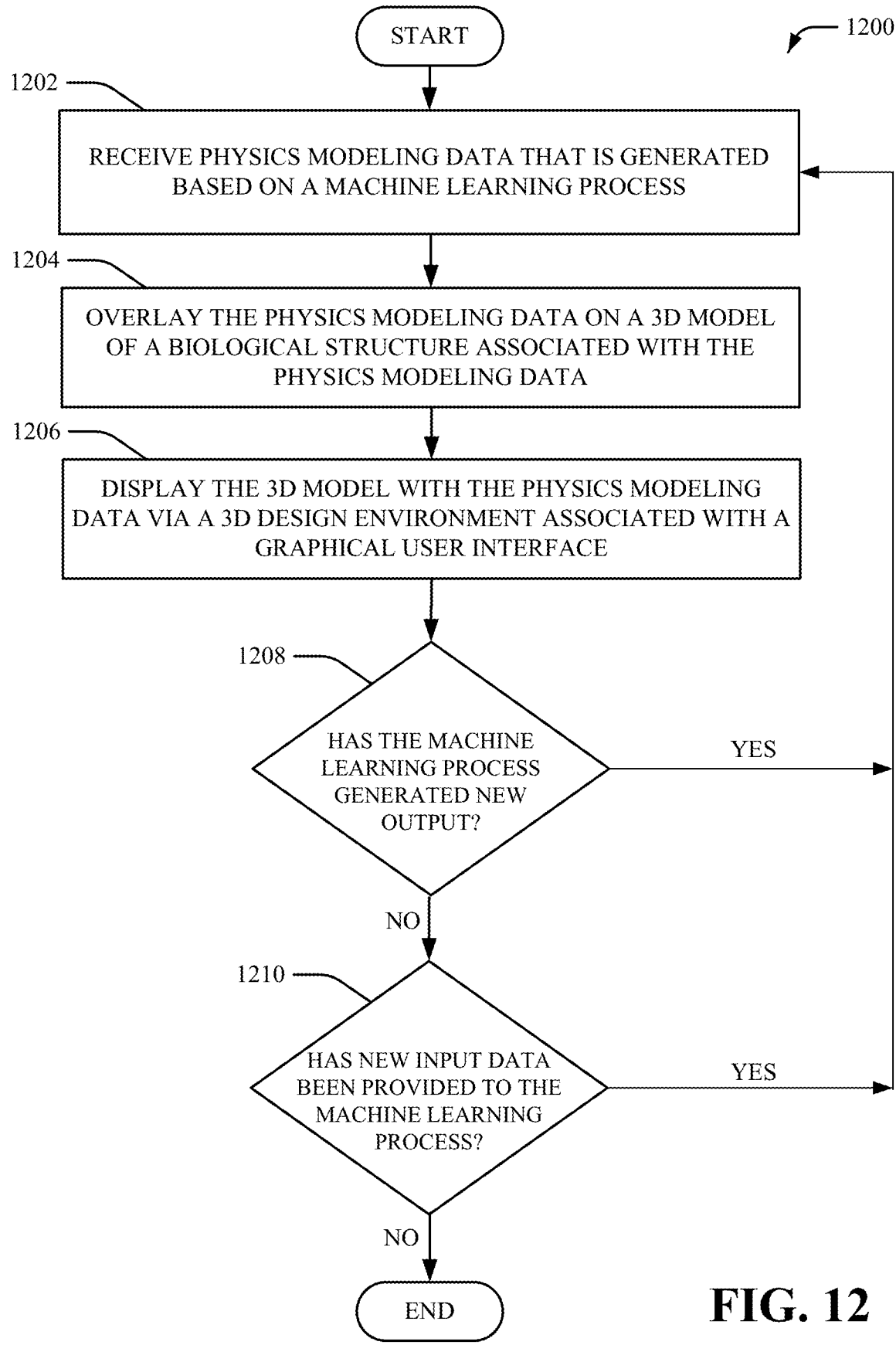
FIG. 12 depicts a flow diagram of yet another example method for providing multi-dimensional fluid modeling of a biological structure, in accordance with various aspects and implementations described herein.

Referring to FIG. 12, there illustrated is a methodology 1200 for providing multi-dimensional fluid modeling of a biological structure, according to yet another aspect of the subject innovation. As an example, the methodology 1200 can be utilized in various applications, such as, but not limited to, modeling systems, biological structure systems, cloud-based systems, medical systems, diagnostics systems, prognostics systems, medical biological structure systems, medical imaging systems, medical modeling systems, health assessment systems, simulation systems, enterprise systems, enterprise imaging solution systems, medical testing systems, advanced medical tool systems, artificial intelligence systems, machine learning systems, neural network systems, etc. At 1202, physics modeling data that is generated based on a machine learning process is received (e.g., by 3D health assessment component 108). At 1204, the physics modeling data is overlaid (e.g., by 3D health assessment component 108) on a 3D model of a biological structure associated with the physics modeling data. At 1206, the 3D model with the physics modeling data is displayed (e.g., by 3D health assessment component 108) via a 3D health assessment environment associated with a graphical user interface. At 1208, it is determined (e.g., by machine learning component 106) whether the machine learning process has generated new output data. If yes, the methodology 1200 returns to 1202 (e.g., to update the physics modeling data). If no, the methodology 1200 proceeds to 1210. At 1210, it is determined (e.g., by machine learning component 106) whether new input data has been provided to the machine learning process. The new input data can be, for example, a new set of parameters for a fluid capable of flowing through the 3D model, a new a set of parameters for a thermal energy capable of flowing through the 3D model, a new a set of parameters for a combustion chemical reaction capable of flowing through the 3D model, and/or another new set of parameters for input provided to the 3D model. If yes, the methodology 1200 returns to 1202 (e.g., to update the physics modeling data). If no, the methodology 1200 can end.

Figure 13:
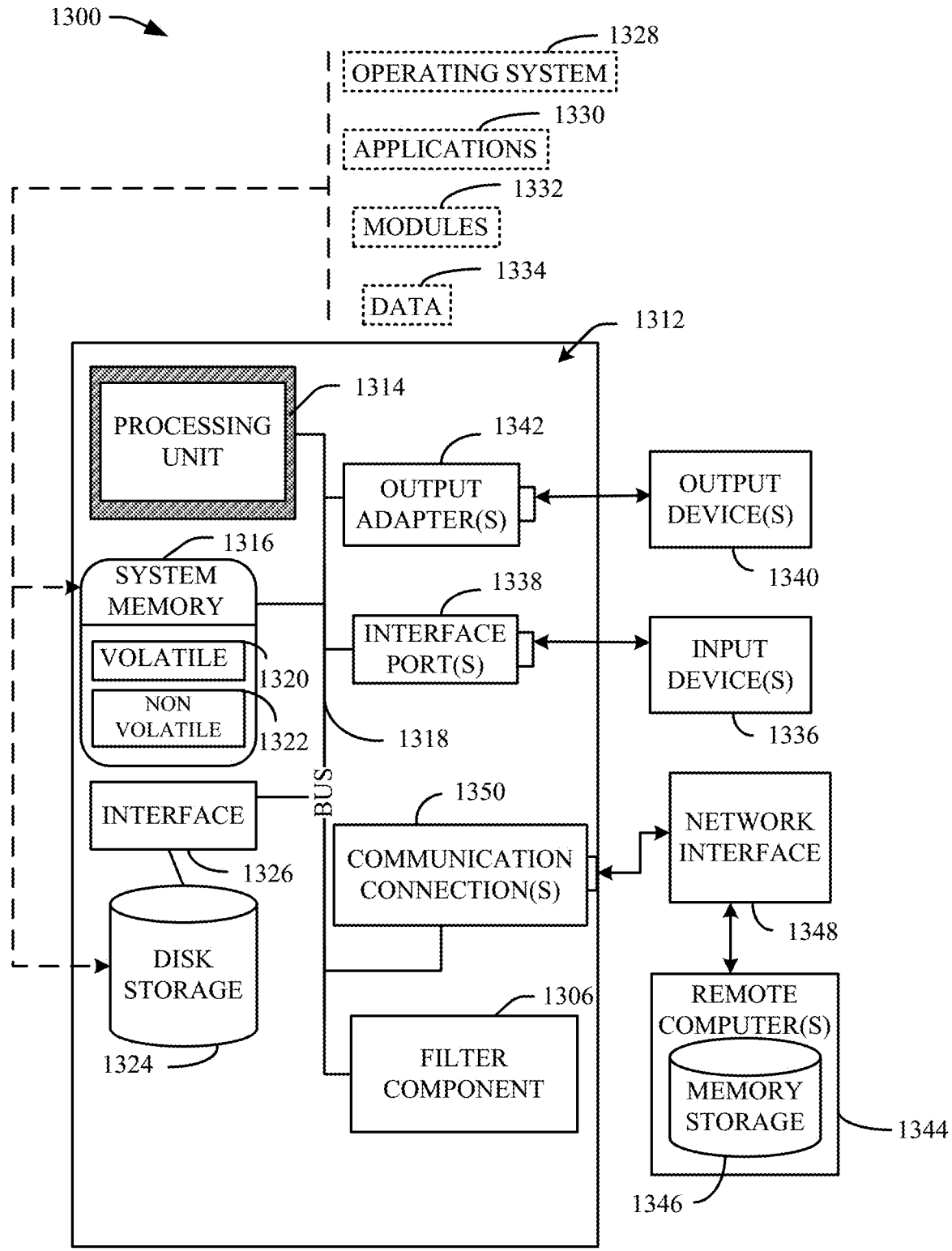
FIG. 13 is a schematic block diagram illustrating a suitable operating environment.
Figure 14:
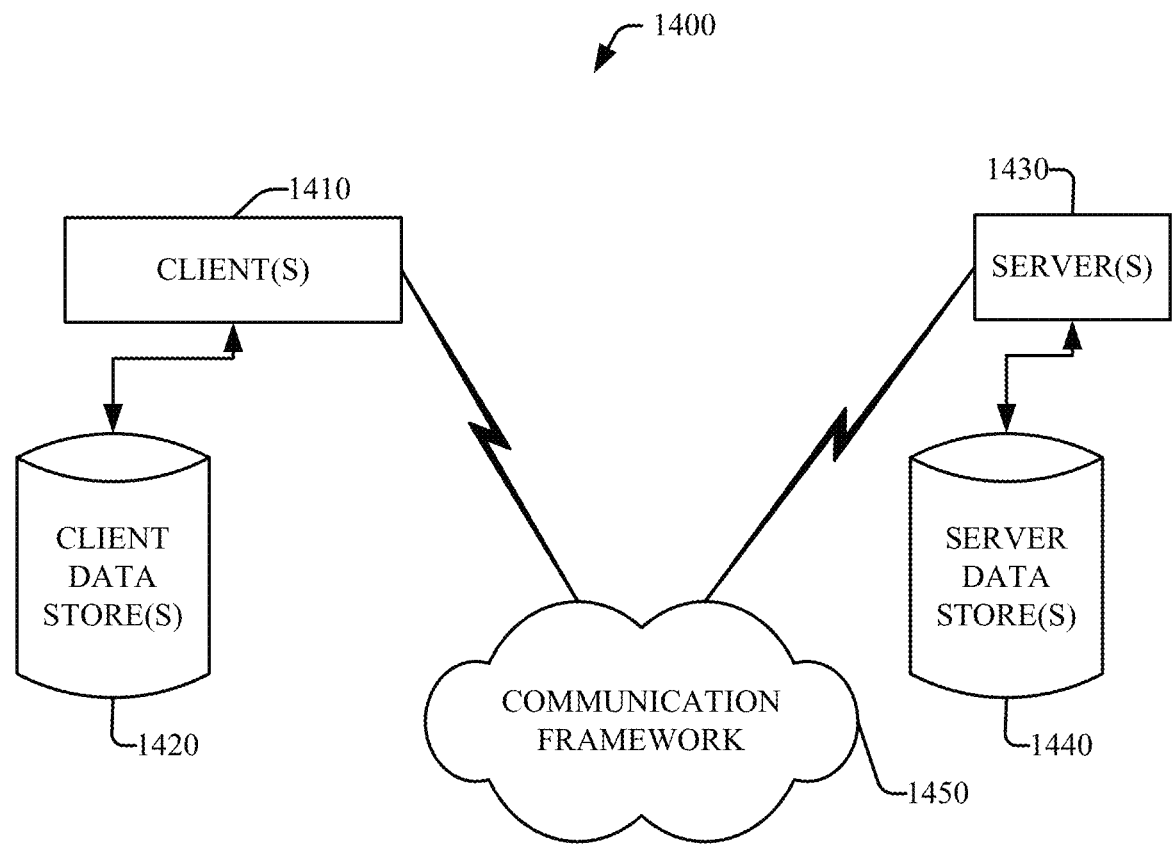
FIG. 14 is a schematic block diagram of a sample-computing environment.

In order to provide a context for the various aspects of the disclosed subject matter, FIGS. 13 and 14 as well as the following discussion are intended to provide a brief, general description of a suitable environment in which the various aspects of the disclosed subject matter may be implemented.

With reference to FIG. 13, a suitable environment 1300 for implementing various aspects of this disclosure includes a computer 1312. The computer 1312 includes a processing unit 1314, a system memory 1316, and a system bus 1318. The system bus 1318 couples system components including, but not limited to, the system memory 1316 to the processing unit 1314. The processing unit 1314 can be any of various available processors. Dual microprocessors and other multiprocessor architectures also can be employed as the processing unit 1314.

The system bus 1318 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1316 includes volatile memory 1320 and nonvolatile memory 1322. The basic input/output system (BIOS), containing the basic routines to transfer information between elements within the computer 1312, such as during start-up, is stored in nonvolatile memory 1322. By way of illustration, and not limitation, nonvolatile memory 1322 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1320 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1312 also includes removable/non-removable, volatile/nonvolatile computer storage media. FIG. 13 illustrates, for example, a disk storage 1324. Disk storage 1324 includes, but is not limited to, devices like a magnetic disk drive, floppy disk drive, tape drive, Jaz drive, Zip drive, LS-100 drive, flash memory card, or memory stick. The disk storage 1324 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1324 to the system bus 1318, a removable or non-removable interface is typically used, such as interface 1326.

FIG. 13 also depicts software that acts as an intermediary between users and the basic computer resources described in the suitable operating environment 1300. Such software includes, for example, an operating system 1328. Operating system 1328, which can be stored on disk storage 1324, acts to control and allocate resources of the computer system 1312. System applications 1330 take advantage of the management of resources by operating system 1328 through program modules 1332 and program data 1334, e.g., stored either in system memory 1316 or on disk storage 1324. It is to be appreciated that this disclosure can be implemented with various operating systems or combinations of operating systems.

A user enters commands or information into the computer 1312 through input device(s) 1336. Input devices 1336 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1314 through the system bus 1318 via interface port(s) 1338. Interface port(s) 1338 include, for example, a serial port, a parallel port, a game port, and a universal serial bus (USB). Output device(s) 1340 use some of the same type of ports as input device(s) 1336. Thus, for example, a USB port may be used to provide input to computer 1312, and to output information from computer 1312 to an output device 1340. Output adapter 1342 is provided to illustrate that there are some output devices 1340 like monitors, speakers, and printers, among other output devices 1340, which require special adapters. The output adapters 1342 include, by way of illustration and not limitation, video and sound cards that provide a means of connection between the output device 1340 and the system bus 1318. It should be noted that other devices and/or systems of devices provide both input and output capabilities such as remote computer(s) 1344.

Computer 1312 can operate in a networked environment using logical connections to one or more remote computers, such as remote computer(s) 1344. The remote computer(s) 1344 can be a personal computer, a server, a router, a network PC, a workstation, a microprocessor based appliance, a peer device or other common network node and the like, and typically includes many or all of the elements described relative to computer 1312. For purposes of brevity, only a memory storage device 1346 is illustrated with remote computer(s) 1344. Remote computer(s) 1344 is logically connected to computer 1312 through a network interface 1348 and then physically connected via communication connection 1350. Network interface 1348 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1350 refers to the hardware/software employed to connect the network interface 1348 to the bus 1318. While communication connection 1350 is shown for illustrative clarity inside computer 1312, it can also be external to computer 1312. The hardware/software necessary for connection to the network interface 1348 includes, for exemplary purposes only, internal and external technologies such as, modems including regular telephone grade modems, cable modems and DSL modems, ISDN adapters, and Ethernet cards.

FIG. 14 is a schematic block diagram of a sample-computing environment 1400 with which the subject matter of this disclosure can interact. The system 1400 includes one or more client(s) 1410. The client(s) 1410 can be hardware and/or software (e.g., threads, processes, computing devices). The system 1400 also includes one or more server(s) 1430. Thus, system 1400 can correspond to a two-tier client server model or a multi-tier model (e.g., client, middle tier server, data server), amongst other models. The server(s) 1430 can also be hardware and/or software (e.g., threads, processes, computing devices). The servers 1430 can house threads to perform transformations by employing this disclosure, for example. One possible communication between a client 1410 and a server 1430 may be in the form of a data packet transmitted between two or more computer processes.

The system 1400 includes a communication framework 1450 that can be employed to facilitate communications between the client(s) 1410 and the server(s) 1430. The client(s) 1410 are operatively connected to one or more client data store(s) 1420 that can be employed to store information local to the client(s) 1410. Similarly, the server(s) 1430 are operatively connected to one or more server data store(s) 1440 that can be employed to store information local to the servers 1430.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing biological structures, mainframe computers, as well as personal computers, hand-held computing biological structures (e.g., PDA, phone), microprocessor-based or programmable consumer or industrial electronics, and the like. The illustrated aspects may also be practiced in distributed computing environments where tasks are performed by remote processing biological structures that are linked through a communications network. However, some, if not all aspects of this disclosure can be practiced on stand-alone computers. In a distributed computing environment, program modules may be located in both local and remote memory storage biological structures.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable biological structure, carrier, or storage media. For example, computer readable storage media can include but are not limited to magnetic storage biological structures (e.g., hard disk, floppy disk, magnetic strips . . . ), optical discs (e.g., compact disc (CD), digital versatile disc (DVD), blu-ray disc (BD) . . . ), smart cards, and flash memory biological structures (e.g., card, stick, key drive . . . ), or the like.

As it is employed in the subject specification, the term "processor" can refer to substantially any computing processing unit or biological structure comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic biological structure (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
    a memory that stores computer executable components; and
    a processor configured to execute the computer executable components stored in the memory, the computer executable components comprising:
        a modeling component that generates a three-dimensional model of a biological structure based on multi-dimensional medical imaging data, wherein the three-dimensional model comprises a control volume overlaid on the biological structure, and wherein the control volume corresponds to a chamber or a vessel of the biological structure through which fluid flows;
        a machine learning component that predicts at least one characteristic of the biological structure based on input data and a machine learning process result associated with the three-dimensional model; and
        a three-dimensional health assessment component that provides a three-dimensional health assessment environment associated with the three-dimensional model, wherein the three-dimensional health assessment environment renders physics modeling data of the biological structure based on the input data and the at least one characteristic of the biological structure on the three-dimensional model.

2. The system of claim 1, wherein the modeling component generates the three-dimensional model based on an integration of a first three-dimensional model associated with a first biological structure and a second three-dimensional model associated with a second biological structure.

3. The system of claim 2, wherein the machine learning component performs a first machine learning process associated with the first three-dimensional model and a second machine learning process associated with the second three-dimensional model.

4. The system of claim 3, wherein the machine learning component performs the first machine learning process based on data associated with the second three-dimensional model.

5. The system of claim 3, wherein the machine learning component performs the second machine learning process based on data associated with the first three-dimensional model.

6. The system of claim 3, wherein the machine learning component determines first characteristics of the first biological structure via the first machine learning process and second characteristics of the second biological structure via the second machine learning process.

7. The system of claim 6, wherein the machine learning component predicts the at least one characteristics of the biological structure based on the first characteristics of the first biological structure and the second characteristics of the second biological structure.

8. The system of claim 2, wherein the machine learning component facilitates interaction between the first three-dimensional model and the second three-dimensional model based on the input data.

9. The system of claim 1, wherein the three-dimensional health assessment component renders the physics modeling data on the three-dimensional model.

10. The system of claim 1, wherein the input data comprises fluid data indicative of a fluid received by the biological structure, and wherein the three-dimensional health assessment environment renders the physics modeling data of the biological structure based on the fluid data and the one or more characteristics of the biological structure on the three-dimensional model.

11. A method, comprising:
generating, by a system comprising a processor, a three-dimensional model of a biological structure based on multi-dimensional medical imaging data, the generating comprises overlaying a set of control volumes on the biological structure, wherein control volumes of the set of control volumes comprise respective abstractions of respective regions of the biological structure through which fluid flows;
predicting, by the system, fluid flow and physics behavior associated with the three-dimensional model based on input data and a machine learning process result associated with the three-dimensional model; and
rendering, by the system, physics modeling data of the biological structure based on the fluid flow and the physics behavior.

12. The method of claim 11, wherein the rendering comprises providing a three-dimensional design environment associated with the three-dimensional model.

13. The method of claim 11, wherein the predicting comprises predicting thermal characteristics and the physics behavior based on the input data and the machine learning process result, and wherein the rendering comprises rendering the physics modeling data of the biological structure based on the thermal characteristics and the physics behavior.

14. The method of claim 11, wherein the predicting comprises one or more predicting combustion characteristics and the physics behavior based on the input data and the machine learning process result, and wherein the rendering comprises rendering the physics modeling data of the biological structure based on the one or more combustion characteristics and the physics behavior.

15. The method of claim 11, wherein the generating the three-dimensional model comprises integrating a first three-dimensional model associated with a first biological structure and a second three-dimensional model associated with a second biological structure.

16. The method of claim 15, wherein the predicting comprises performing a first machine learning process associated with the first three-dimensional model and performing a second machine learning process associated with the second three-dimensional model.

17. A non-transitory computer readable storage biological structure comprising instructions that, in response to execution, cause a system comprising a processor to perform operations, comprising:
generating a three-dimensional model of a biological structure based on multi-dimensional medical imaging data, wherein the three-dimensional model comprises at least one control volume overlaid on the biological structure, and wherein the at least one control volume is a representation of at least one chamber or at least one vessel of the biological structure through which fluid flows;
performing a machine learning process associated with the three-dimensional model;
predicting one or more characteristics of the biological structure based on the performing the machine learning process; and
providing a three-dimensional design environment associated with the three-dimensional model, the three-dimensional design environment renders physics modeling data of the biological structure based on the machine learning process.

18. The non-transitory computer readable storage biological structure of claim 17, wherein the generating the three-dimensional model comprises combining a first three-dimensional model associated with a first biological structure and a second three-dimensional model associated with a second biological structure.

19. The non-transitory computer readable storage biological structure of claim 18, wherein the performing comprises performing a first machine learning process associated with the first three-dimensional model and performing a second machine learning process associated with the second three-dimensional model.

20. The non-transitory computer readable storage biological structure of claim 19, wherein the performing the first machine learning process comprises performing the first machine learning process based on data associated with the second machine learning process.

* * * * *

UNITED STATES PATENT AND TRADEMARK OFFICE
CERTIFICATE OF CORRECTION

| | | |
|---|---|---|
| PATENT NO. | : 11,004,568 B2 | Page 1 of 1 |
| APPLICATION NO. | : 15/630935 | |
| DATED | : May 11, 2021 | |
| INVENTOR(S) | : Dweik et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 358 days.

Signed and Sealed this
Twenty-fifth Day of October, 2022

*Katherine Kelly Vidal*

Katherine Kelly Vidal
*Director of the United States Patent and Trademark Office*